US008686225B2

(12) United States Patent
Huang et al.

(10) Patent No.: US 8,686,225 B2
(45) Date of Patent: *Apr. 1, 2014

(54) MONOCOT SEED PRODUCT COMPRISING A HUMAN BLOOD PROTEIN

(75) Inventors: Ning Huang, Davis, CA (US); Raymond L. Rodriguez, Davis, CA (US); Frank E. Hagie, Sacramento, CA (US); David M. Stalker, Woodland, CA (US)

(73) Assignee: Ventria Bioscience Inc., Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/449,233

(22) Filed: Apr. 17, 2012

(65) Prior Publication Data

US 2012/0195883 A1 Aug. 2, 2012

Related U.S. Application Data

(60) Division of application No. 12/751,869, filed on Mar. 31, 2010, now Pat. No. 8,158,857, which is a continuation of application No. 11/987,053, filed on Nov. 27, 2007, now abandoned, which is a division of application No. 10/411,395, filed on Apr. 11, 2003, now Pat. No. 7,304,208, which is a continuation-in-part of application No. 10/077,381, filed on Feb. 14, 2002, now Pat. No. 6,991,824, which is a continuation-in-part of application No. 09/847,232, filed on May 2, 2001, now abandoned.

(60) Provisional application No. 60/269,199, filed on Feb. 14, 2001, provisional application No. 60/266,920, filed on Feb. 6, 2001, provisional application No. 60/201,182, filed on May 2, 2000.

(51) Int. Cl.
C12N 15/82 (2006.01)
A23L 1/0526 (2006.01)
A23L 1/10 (2006.01)
A61K 35/14 (2006.01)
A61K 35/16 (2006.01)
C07K 16/00 (2006.01)

(52) U.S. Cl.
USPC .......... 800/288; 800/287; 800/295; 800/298; 426/615; 426/618; 426/622; 530/362; 530/363; 530/380; 530/381; 530/382; 530/383; 530/384; 530/385; 530/386; 530/387.1

(58) Field of Classification Search
None
See application file for complete search history.

(56) References Cited

U.S. PATENT DOCUMENTS

| | | |
|---|---|---|
| 5,202,422 A | 4/1993 | Hiatt et al. |
| 5,639,947 A | 6/1997 | Hiatt et al. |
| 5,763,748 A | 6/1998 | Sijmons et al. |
| 5,767,363 A | 6/1998 | De Silva et al. |
| 5,959,177 A | 9/1999 | Hein et al. |
| 5,994,628 A | 11/1999 | Rodriguez |
| 6,303,341 B1 | 10/2001 | Hiatt et al. |
| 6,344,600 B1 | 2/2002 | Merot et al. |
| 6,471,429 B1 | 10/2002 | Isobe et al. |
| 6,569,831 B1 | 5/2003 | Legrand et al. |
| 6,991,824 B2 | 1/2006 | Huang et al. |
| 7,138,150 B2 | 11/2006 | Huang et al. |
| 7,417,178 B2 | 8/2008 | Huang et al. |
| 7,718,851 B2 | 5/2010 | Huang et al. |
| 2002/0046418 A1 | 4/2002 | Hooker et al. |
| 2002/0078472 A1 | 6/2002 | Christou et al. |
| 2002/0174453 A1 | 11/2002 | Daniell et al. |
| 2003/0056244 A1 | 3/2003 | Huang et al. |
| 2010/0003235 A1 | 1/2010 | Hagie et al. |
| 2010/0015713 A1 | 1/2010 | Deeter et al. |
| 2010/0031394 A1 | 2/2010 | Huang et al. |
| 2010/0119691 A1 | 5/2010 | Huang et al. |

FOREIGN PATENT DOCUMENTS

| | | |
|---|---|---|
| WO | WO 99/16890 A2 | 4/1999 |
| WO | WO 02/064750 A2 | 8/2002 |
| WO | WO 02/099067 A2 | 12/2002 |

OTHER PUBLICATIONS

Nakase et al. Rice DNA for 26 kDa globulin, complete cds. (1999) GenBank Accession D50643.1; pp. 1-2.*
Allen, "Opportunities for the Use of Aerosolized α-1-antitrypsin for the Treatment of Cystic Fibrosis", Chest, vol. 110, pp. 256s-260s (1996).
Beatty et al., "Kinetics of Association of Serine Proteinase with native and Oxidized α-1-antichymotrypsin", J. Biol. Chem. 255, pp. 3931-3934 (1980).
Bednarek et al., "Intracellular Trafficking of Secretory Proteins", Plant Mol. Biol., vol. 20, pp. 133-150 (1992).
Bingle et al., "Secretory Leukoprotease Inhibitor; Partnering α-1-proteinase Inhibitor to Combat Pulmonary Inflammation", Thorax., vol. 51, pp. 1273-1274 (1996).
Brennan et al., "Circulating Proalbumin associated with a Variant Proteinase Inhibitor", Biochem. Biophys. Acta, vol. 802, pp. 24-28 (1984).
Brown et al., "The Crystal Structure of Modified Bovine Fibrinogen", Proc. Nat'l. Acad. Sci., vol. 97, pp. 85-90 (2000).
Carrell et al., "Human α-1-antitrypsin: Carbohydrate Attachment and Sequence Homology", FEBS Letters vol. 135, pp. 301-303 (1981).
Carrell et al., "Structure and Variation of Human α-1-antitrypsin", Nature, vol. 298, pp. 329-334 (1982).

(Continued)

Primary Examiner — Cathy Kingdon Worley
(74) Attorney, Agent, or Firm — Susan J. Myers Fitch; McDermott Will & Emery LLP

(57) ABSTRACT

The invention is directed to blood proteins produced in monocot seeds and isolated therefrom for use in therapeutic compositions, as well as to methods of making these isolated blood proteins and to therapeutic compositions comprising them.

16 Claims, 11 Drawing Sheets

(56) References Cited

OTHER PUBLICATIONS

Chrispeels, "Sorting Proteins in the Secretory System", Annu. Rev. Plant. Physiol. Plant Mol. Biol. vol. 42, pp. 21-53 (1991).
Chrispeels and Raikhel, (1992). "Short peptide domains target proteins to plant vacuoles", Cell vol. 68, pp. 613-616 (1992).
Christou, "Genetic Transformation of Crop Plants using Microprojectile Bombardment", Plant J., vol. 2, pp. 275-281 (1992).
Daniell et al., "Medical molecular farming: production of antibodies, biopharmaceuticals and edible vaccines in plants", Trends in Plant Science, vol. 6, No. 5, pp. 219-226 (2001).
Davidson et al., "Persistence of Human Milk Proteins in the Breast-fed Infant", Act Pediatric. Scand., vol. 76, pp. 733-740 (1987).
Ditta et al., "Broad host range DNA cloning system from gram-negative bacteria: Construction of a gene bank from Rhizobium meliloti", Proc. Natl. Acad. Sci. USA, vol. 77, pp. 7347-7351 (1980).
Dowd et al., "Effective treatment with α-1-protease inhibitor of chronic cutaneous vasculitis associated with α-1-antitrypsin deficiency", J. Am. Acad. Dermatol., vol. 33, pp. 913-916 (1995).
Eriksson, "Pulmonary Emphysema and α-1-Antitrypsin Deficiency", Acta Medic Scand., vol. 175, pp. 197-205 (1964).
Everse et al., "Conformational changes in fragments D and doubl-D from human fibrinogen upon binding the peptide ligan Gly-His-Pro-amide", Biochemistry, vol. 38, pp. 2941-2946 (1999).
Farran et al., "Targeted expression of human serum albumin to potato tubers", Transgenic Research, vol. 11, pp. 337-346 (2002).
Friezner-Degen et al., "Characterization of the complementary deoxyribonucleic acid and gene coding for human prothrombin", Biochemistry, vol. 22, pp. 2087-2097 (1983).
Hiatt et al., "Production of antibodies in transgenic plants", Nature, vol. 342, pp. 76-78 (1989).
Hiatt and Ma, "Monoclonal antibody engineering in plants", FEBS Letters, vol. 307, pp. 71-75 (1992).
Holmberg et al., "Transgenic tobacco expressing Vitreoscilla hemo-globin exhibits enhanced growth and altered metabolite production", Nature Biotech., vol. 15, pp. 244-247 (1997).
Horvath et al., "The production of recombinant proteins in transgenic barley grains", Proc. Natl. Acad. Sci., vol. 97, No. 4, pp. 1914-1919 (2000).
Huang et al., "Expression and Purification of Functional Human α-1-Antitrypsin from Cultures Plant Cells", Biotechnology Prog., vol. 17, pp. 126-133 (2001).
Huang et al., "Codon usage patterns in plant genes", J. CAASS, vol. 1, pp. 73 (1990).
Huang et al., "The tissue-specific activity of a rice B-glucanase promoter (Gns9) is used to select rice transformants", Plant Sci., vol. 161, pp. 589-595 (2001).
Hubbard et al., "Recombinant DNA-produced α-1-antitrypsin administered by aerosol augments lower respiratory tract antineutrophil elastase defenses in individuals with α-1-antitrypsin deficiency", J. Clinical Invest., vol. 84, pp. 1349-1354 (1989).
Jouanin et al., "Localization and restriction maps of the replication origin regions of the plasmids of Agrobacterium rhizogenes strain $A_4$", Mol, Gen, Genet., vol. 201, pp. 370-374 (1985).
Judah et al., "Biosynthesis of serum albumin in rat liver, evidence for the exsistance of 'proalbumin'", Biochem. J., vol. 134, pp. 1083-1091 (1973).
Kurachi et al., "Cloning and sequence of a cDNA coding for α-1-antitrypsin", Proc. Nat. Acad. Sci., vol. 78, pp. 6826-6830 (1981).
Ma et al., "Generation and assembly of Secretory Antibodies in plants", Science, vol. 268, pp. 716-719 (1995).
Ma et al., "Antibody Production and Engineering in Plants" Annals of the New York Acad. of Sciences, vol. 25, pp. 72-81 (1996).
Madrazo et al., "Crystal structure of the central region of bovine fibrinogen E5 fragment at 1.4 A resolution", Proc. Nat. Acad. Sci., vol. 98, pp. 11967-11972 (2001).
Mankad and Codispoti, "The role of fibrin sealants in hemostasis", Am. J. Surg., vol. 182, pp. 21s-28s (2001).

McBride and Summerfelt, "Improved binary vectors for Agrobacterium mediated plant transformation", Plant Mol. Biol., vol. 14, pp. 269-276 (1990).
McElvaney et al., "Aerosol α-1-antitrypsin treatment for cystic fibrosis", The Lancet, vol. 337, pp. 392-394 (1991).
McGilligan et al., "α-1-antitrypsin concentration in human milk", Pediatr. Res., vol. 22, pp. 268-270 (1987).
Newman, "Serum-free cell culture—the ethical, scientific and economic choice", The Biomedical Scientist, pp. 941-942 (2003).
O'Riordan et al., "α-1-antitrypsin deficiency-associated panniculitis", Transplant, vol. 63, pp. 480-482 (1997).
Panahi et al., "Recombinant protein expression plasmids optimized for industrial E. coli fermentation and plant systems produce biologically active human insulin-like growth factor-1 in transgenic rice and tobacco plants", Transgenic Research, vol. 13, pp. 245-259 (2004).
Rabiet et al., "Prothrombin fragment 1*2*3; a major product of prothrombin activation in human plasma", J. Biol. Chem., vol. 261, pp. 13210-13215 (1986).
Rosenberg et al., "Activation of human prothrombin by highly purified human factors V and Xa in the presence of human antithrombin", J. Biol. Chem., vol. 250, pp. 1607-1617 (1975).
San Millan et al., "A chloroplast transgenic approach to hyper-express and purify Human Serum Albumin, a protein highly susceptible to proteolytic degradation", Plant Biotechnology Journal, vol. 1, pp. 71-79 (2003).
Sardana et al., "Biological activity of human granulocyte-macrophage colony stimulating factor is maintained in fusion with seed glutelin peptide", Transgenic Research, vol. 11, pp. 521-531 (2002).
Sandhaus, "α-1-antitrypsin Augmentation Therapy in Proteases, Protease Inhibitors and Protease-Derived Peptides", Birkhauser Verlag, Basel, pp. 97-102 (1993).
Sanford et al., "Optimizing the biolistic process for different biological applications", Meth. Enzymol., vol. 217, pp. 83-509 (1993).
Shieh et al., "Nuclear targeting of the maize R protein requires two nuclear localization sequences", Plant Physiol., vol. 101, pp. 353-361 (1993).
Sijmons et al., "Production of correctly processed human serum albumin in transgenic plants", Bio/Technology, vol. 8, pp. 217-221 (1990).
Smeekens et al., "The role of the transit peptide in the routing of precursors towards different chloroplast compartments", Cell, vol. 46, pp. 365-376 (1986).
Spotnitz, "Commercial fibrin sealants in surgical care", Am. J. Surg., 182, pp. 8s-14s (2001).
Travis and Salvesen, "Human plasma proteinase inhibitors", Annu. Rev. Biochem., vol. 52, pp. 655-709 (1983).
Vine et al., "Assembly and plasma membrane targeting of recombinant immunoglobin chains in plants with a murine immunoglobin transmembrane sequence", Plant Molec. Biol., vol. 45, pp. 159-167 (2001).
Varagona et al., "Nuclear-localization signals required for nuclear targeting of the maize regulatory protein, Opaque-2", Plant Cell, vol. 4, pp. 1213-1227 (1992).
Vitale and Chrispeels, "Sorting of proteins to the vacuoles of plant cells", BioEssays, vol. 14, pp. 151-160 (1992).
Wasmann et al., "The importance of the transit peptides and the transported protein for protein import into chloroplasts", Mol. Gen. Genet., vol. 205, pp. 446-453 (1986).
Weeke and Krasilnikoff, "A polynomial expression for the serum concentrations of 21 serum proteins from 1 to 93 years of age in normal males and females", Protein Biol. Fluids, vol. 18, pp. 173-179 (1971).
Yakovlev et al., "Role of the β-strand in the central domain of fibrinogen gamma module", Biochemistry, vol. 39, pp. 15721-15729 (2000).
Yang et al., "Crystal structure of native chicken fibrinogen at 5.5 A resolution", Proc. Nat. Acad. Sci., vol. 97, pp. 3907-3912 (2000).
Zhang et al., "Expression and production of bioactive human interleukin-18 in transgenic tobacco plants", Biotechnology Letters, vol. 25, pp. 1629-1635 (2003).

* cited by examiner

Panel A

Panel B

Panel A. Kinetics of elastase inhibition by AAT

Panel B. AAT Thermostability

Native human AAT ─□─
Rice recombinant AAT ---○---

MONOCOT SEED PRODUCT COMPRISING A HUMAN BLOOD PROTEIN

REFERENCE TO RELATED APPLICATIONS

This application is a divisional application of U.S. patent application Ser. No. 12/751,869, filed Mar. 31, 2010, now issued as U.S. Pat. No. 8,158,857, which is a continuation application of U.S. patent application Ser. No. 11/987,053, filed Nov. 27, 2007, now abandoned, which is a divisional of U.S. patent application Ser. No. 10/411,395, filed Apr. 11, 2003, now U.S. Pat. No. 7,304,208, which, in turn, is a continuation-in-part of U.S. application Ser. No. 10/077,381, filed Feb. 14, 2002, now U.S. Pat. No. 6,991,824, which claims priority benefit to U.S. provisional application Ser. No. 60/269,199, filed Feb. 14, 2001, application Ser. No. 10/077,381 being a continuation-in-part of U.S. patent application Ser. No. 09/847,232, filed May 2, 2001, now abandoned, which claims priority benefit to U.S. provisional application Ser. No. 60/266,920, filed Feb. 6, 2001, and U.S. provisional application Ser. No. 60/201,182, filed May 2, 2000. All priority applications are incorporated herein by reference in their entirety.

REFERENCE TO SEQUENCE LISTING, TABLE OR COMPUTER PROGRAM

A "Sequence Listing" is submitted with this application in the form of a text file, created 17 Apr. 2012, and named "506658027US04seqlist.txt" (22,510 bytes), the contents of which are incorporated herein by reference in their entirety.

FIELD OF THE INVENTION

The present invention relates to human blood proteins produced in the seeds of monocot plants for use in making human and animal topical compositions and human therapeutic compositions.

BACKGROUND OF THE INVENTION

Many human blood proteins are in short or limited supply due to the larger quantities required of the protein for positive therapeutic effect or possibly also due to the larger demand of these proteins by the world population of patients having the particular condition. It is also advantageous to produce blood proteins, normally extracted from blood products, from an alternative source such as crop plants. Production of blood proteins from plants mitigates contamination of the blood protein fraction with human viruses and other disease causative agents found in human or animal blood product fractions.

Blood proteins such as hemoglobin, alpha-1-antitrypsin ("AAT"), fibrinogen, human serum albumin, thrombin, antithrombin III, antibodies, blood coagulation factors (e.g. Factors V-XIII), and others are known to have therapeutic potential for a number of human conditions.

Hemoglobin is the major blood component molecule transporting oxygen to cells. Mammmalian hemoglobins are tetrameric proteins made up of two ex-like polypeptide subunits and two non-α (usually β, γ, or δ) subunits. These subunits differ in primary amino acid sequence, but have similar secondary and tertiary structures. Each globin subunit has associated with it, by noncovalent interaction, a $Fe^{2+}$-porphyrin complex known as a heme group, to which oxygen binds. The predominant hemoglobin in adult erythrocytes is α2β2, known as hemoglobin $A_1$ (HbA). Each hemoglobin tetramer has a molecular weight of 64 kD and each α-like and β-like chain has a molecular weight of approximately 15.7 kD (141 amino acids) and 16.5 kD (146 amino acids) respectively.

AAT belongs to the class of serpin inhibitors and is one of the major protease inhibitors in human plasma. AAT is a single 394 amino acid polypeptide having an approximate molecular mass of 52 kD, and contains about 15% carbohydrate in the native human form of the molecule. Concentrations of AAT in human plasma range from 1000-3000 mg/L and in human milk range from 100 to 400 mg/L Its primary physiological role is the inhibition neutrophil elastase, with an insufficiency leading to the development of pulmonary emphysema. Excess production of elastase activity leads to emphysema, hepatitis and a variety of skin disorders. While the binding affinity of AAT is highest for human neutrophil elastase, it also has affinity for pancreatic proteases such as chymotrypsin and trypsin. The current primary source for the treatment of AAT deficiency is isolating AAT from human blood plasma.

Fibrinogen is involved in the blood coagulation cascade and is converted to fibrin by its interaction with the natural clotting agent thrombin. Fibrin is the major component of blood clotting. Mature human fibrinogen consists of two pairs of three independent polypeptide chains (α, β and γ) that are linked together by 29 intra- and intermolecular disulfide bonds forming a native protein of 340 kD and is present in human plasma at an approximate concentration of 2500 mg/L. Three-dimensional structural analysis of independent fibrinogen domains has provided detailed structural features giving important clues to human fibrinogen's multifunctional role. The fibrinogen polypeptides are approximately 72 kD (α), 52 kD (β) and 48 kD (γ) respectively with the β polypeptide chain determining native molecule assembly. The structure of fibrinogen features a number of structural and functional domains containing multiple binding sites that facilitate interactions with itself, other proteins, certain cell types and allow fibrinogen to participate in a number of important physiological processes including blood coagulation, inflammation, angiogenesis, wound closure, artheriogenesis and tumorigenesis. Fibrin formation from a clotting standpoint is mediated by the interaction of native fibrinogen with its natural clotting agents Factor XIII and thrombin in the presence of blood soluble calcium.

Albumin is a transport protein molecule that carries out many functions in mammalian serum biology, notably that of a carrier of hormones and other soluble ligands from site to site, and other activities that contribute largely to general mammalian biochemistry. Human serum albumin ("HSA") is also the major protein component of blood being actively present at serum concentrations of approximately 30,000-50,000 mg/L. HSA is a single polypeptide chain of 66.5 kD that is initially synthesized as a prepro-albumin molecule in the liver and released from the endoplasmic reticulum after N-terminal and C-terminal Golgi processing. The resultant mature protein is 585 amino acids in length. It has been shown that the natural preprosequnce of HSA can function in correct protein targeting/processing across a plant plasma membrane in transgenic tobacco leaves (Sijmons et al., 1990).

Prothrombin, a plasma glycoprotein, is the zymogen of the serine protease thrombin that catalyzes the conversion of fibrinogen to fibrin as well as several other reactions that may be important for blood coagulation. Prothrombin is a single polypeptide chain approximately 72,000 molecular weight in size. The complete human thrombin cDNA consists of 622 amino acid residues and includes a leader sequence of 36 amino acid residues. Active thrombin has an apparent molecular weight of 36,000 and is made up of two disulfide-linked polypeptide chains resulting from prothrombin cleavage. The proteolytic events leading to in vitro activation and conversion of human prothrombin to active thrombin have been extremely well characterized. Antithrombin III is a single chain glycoprotein with a molecular weight of 58 kD. It is a member of the serpin (serine protease inhibitor) super family and is considered to be the most important inhibitor in the coagulation cascade. Antithrombin III inhibits a wide spectrum of serine proteases including thrombin, factors IXa, Xa and XIa, kallikrein, plasmin, urokinase, C1-esterase, and trypsin. Antithrombin III activity is markedly potentiated by heparin; potentiation of its activity is the principle mechanism by which both heparin and low-molecular-weight heparin produce anticoagulation.

Factors V-XIII are proteins (mostly proteases in their active states) that are involved in the 'intrinsic pathway' of the classical casade mechanism for blood coagulation. The majority of these molecules exist as precursors that are processed in an ordered sequence of transformations from inactive to catalytically active forms. Factor V is proaccelerin (the accelerator globulin) while Factor VI is the activated form of Factor V. Factor VII is proconvertin, the plasma thromboplastin component, while Factors VIII (antihemophilic factor) and IX (Christmas antihemophilic factor) are both associated with the hemophilia disease state. Factors X (Stuart-Power factor), XI (plasma thromboplastin anticedent) and XII (Hageman factor) are all involved with the maturation/stabilization of thrombin. Factor XIII (fibrin stabilizing factor) is a plasma transglutaminase directly acting on fibrin during the clotting process. All these Factors are present at relatively low in serum plasma (0.001 to 50 mg/L). Other protein factors also involved in the blood coagulation cascade include Fletcher Factor (prekallikrein), Fitzgerald factor (kininogen) and von Willebrand Factor.

Immunoglobulins (antibodies) present in humans act to confer resistance to a variety of pathogens to which a patient may have been exposed. Immunoglobulin molecules account for 15-20% of the mass in human serum and consist predominantly of IgG, IgM and IgA-type antibodies involved in fighting various infections that invade the blood system and potentially the rest of the body. IgG type antibodies are the most prevalent and exist at a serum concentration of between 618 g/L. The blood system also serves as a carrier directing these molecules to specific areas of the body to combat resulting infections and potential oncogenic targets. Mature antibodies consist of two polypeptides (light and heavy chains) that must be expressed in eqimolar amounts and come together to form functional entities. The light chain (~25 kD) is a protein of ~210-240 amino acids in length while the heavy chain (~50 kD) is a protein of ~450-460 amino acids in length. Both light and heavy chains carry signal peptides for processing and secretion into the blood stream. Expression of monoclonal antibodies in plants is of particular interest, because it requires the expression of two genes, synthesis of two proteins and correct assembly of the tetrameric protein to result in a functional antibody.

Initial studies of antibodies in plants focused on the IgG antibody class (Hiatt et al., 1989; Hiatt and Ma, 1992), but later studies explored the in planta expression of complex antibody molecules such as secretory IgA antibodies (4 genes) and more complex antibody forms (Ma et al., 1995; Vine et al., 2001).

US. Pat. Nos. 6,471,429, 5,959,177, 5,639,947 and 5,202,422, all related patents, disclose the production of antibody molecules in transgenic tobacco plant leaves.

U.S. Pat. No. 6,303,341 discloses the production of immunoglobulins containing protection proteins in tobacco plant leaves, stems, flowers and roots.

Published U.S. Patent Application U.S. 2002/0174453 discloses the production of antibodies in the plastids of tobacco plants.

Published U.S. Patent Application U.S. 2002/0046418 discloses a controlled environment agriculture bioreactor for the commercial production of heterologous proteins in transgenic plants. The specification discloses that production of mammalian blood proteins can be achieved. Example 7 discloses the production of human blood factors in the leaves of potato, tobacco and alfalfa plants.

U.S. Pat. No. 6,344,600 discloses the production of hemoglobin and myoglobin in tobacco plant leaves. Example X discloses the extraction and partial purification of recombinant hemoglobin from tobacco seeds. The expression was obtained by transformation of the coexpression plasmid pBIOC59, which was constructed to allow targeting in the chloroplasts, and contained for this purpose the transit peptide of the precursor of the small subunit of ribulose 1,5-diphosphate carboxylase of *Pisum sativum* L. Expression in seeds was reported to be at a maximum level of 0.05% recombinant hemoglobin relative to the total soluble proteins extracted.

Example XI of the '600 patent discloses the construction of plasmids containing one of the α or β chains of hemoglobin allowing constitutive expression or expression in the albumin in maize seeds. According to this disclosure, the constitutive or albumin-specific expression of the hemoglobin chains required the following regulatory sequences: one of three promoters allowing a constitutive expression ((i) the rice actin promoter followed by the rice actin intron, contained in the plasmid pAct1-F4; (ii) the 35S double constitutive promoter of cauliflower mosaic virus; or (iii) the promoter of the maize γ-zein gene contained in the plasmid pγ63) and one of two terminators ((i) the 35S polyA terminator; or (ii) the NOS polyA terminator). No experiment or data is provided regarding transformation or expression of these plasmids in maize or maize seeds.

U.S. Pat. No. 5,767,363 discloses the use of a seed-specific promoter derived from ACP of *Brassica napus*, to affect and vary the expression of seed oils in rape and tobacco plants. The specification generically discloses that the seed specific promoter can be used for the expression of pharmaceutical proteins, such as blood factors or human serum albumin, however no experimental data whatsoever is presented in this regard.

Daniell et al. (2001) is a review article discussing recent developments in the field of medical molecular farming, including the production of antibodies and proteins in plants.

None of these patents or publications discloses the production of human blood proteins in monocot seeds in high yield. It is desirable to provide for the production of human blood proteins in high yield free from contaminating source agents in order to provide the patient population with sufficient supply of these proteins for use in treating humans with conditions treatable by administration of a particular blood protein.

SUMMARY OF THE INVENTION

In one aspect, the invention includes a method of producing a recombinant human blood protein in monocot plant seeds, comprising the steps of:
  a. transforming a monocot plant cell with a chimeric gene comprising a promoter from the gene of a maturation-specific monocot plant storage protein, i. (ii) a first DNA sequence, operably linked to said promoter, encoding a monocot plant seed-specific signal sequence capable of targeting a polypeptide linked thereto to a monocot plant seed endosperm cell, and ii. (iii) a second DNA sequence, linked in translation frame with the first DNA sequence, encoding a human blood protein, wherein the first DNA sequence and the second DNA sequence together encode a fusion protein comprising an N-terminal signal sequence and the human blood protein;

b. growing a monocot plant from the transformed monocot plant cell for a time sufficient to produce seeds containing the human blood protein; and c. harvesting the seeds from the plant, wherein the human blood protein constitutes at least 3.0% of the total soluble protein in the harvested seeds.

The invention also includes a purified human blood protein obtained by the method. Preferably, the human blood protein comprises one or more plant glycosyl groups.

The invention also provides a monocot plant seed product, preferably selected from whole seed, flour, extract and malt, prepared from the harvested seeds obtained by the method of the invention. Preferably, the human blood protein constitutes at least 3.0% of the total soluble protein in the seed product.

The invention further provides a composition comprising a purified human blood protein, preferably comprising at least one plant glycosyl group, and at least one pharmaceutically acceptable excipient or nutrient, wherein the human blood protein is produced in a monocot plant containing a nucleic acid sequence encoding the human blood protein and is purified from seed harvested from the monocot plant. The nutrient is from a source other than the monocot plant. The formulation can be used for parenteral, enteric, inhalation, intranasal or topical delivery.

These and other objects and features of the invention will become more fully apparent when the following detailed description of the invention is read in conjunction with the accompanying drawings and claims.

BRIEF DESCRIPTION OF THE FIGURES

FIG. 3A indicates total protein extracted from rice seeds under non-denaturing conditions (350 mM NaCl, PBS pH 7.4, 0.01% Tween-20/Trition X-100/CHAPS) and run on a non-denaturing 10% acrylamide gel. Lane 1, 1 μg purified human fibrinogen; Lanes 2 & 3, extracts from Tapei 309, a nontransgenic rice variety; Lane 4, molecular weight markers; Lanes 5 & 7, extracts from two transgenic rice lines where 1.0% βMe was included in the extraction buffer; lanes 6 & 8, extracts from two transgenic rice lines without βMe in the extraction buffer. Lanes 6 & 8 show large protein aggregates that were extracted under non-denaturing conditions from the transgenic lines that run at the approximate position of complexed native human fibrinogen. FIG. 3B indicates total protein extracted from rice seeds in 2% SDS, 1M urea, 1% βMe and PBS pH 7.4, and run on SDS PAGE. Lane 1, positive control, native human fibrinogen (obtained from the Red Cross) showing all three polypeptide chains; Lane 2, molecular weight standards; Lanes 3-5, three independent transgenic rice lines expressing all three fibrinigen polypeptides.

Lane MW refers to molecular weight markers. Panel 7A: Lane 1, purified non-recombinant AAT from human plasma; Lane 2, purified AAT from human plasma+PPE; Lane 3, soluble protein extract containing AAT from transgenic rice seed; Lane 4, protein extract containing AAT from transgenic rice seed+PPE; Lane 5, non-transformed rice seed extract; Lane 6, non-transformed rice seed extract+PPE. Panel 7B shows a shifted band in Lanes 1, 2 and 3. The shifted band, a complex between PPE and an AAT fragment is confirmed to contain AAT by Western blot analysis. The lanes in Panel 7B are analogous to those in Panel 7A.

Figure 8:
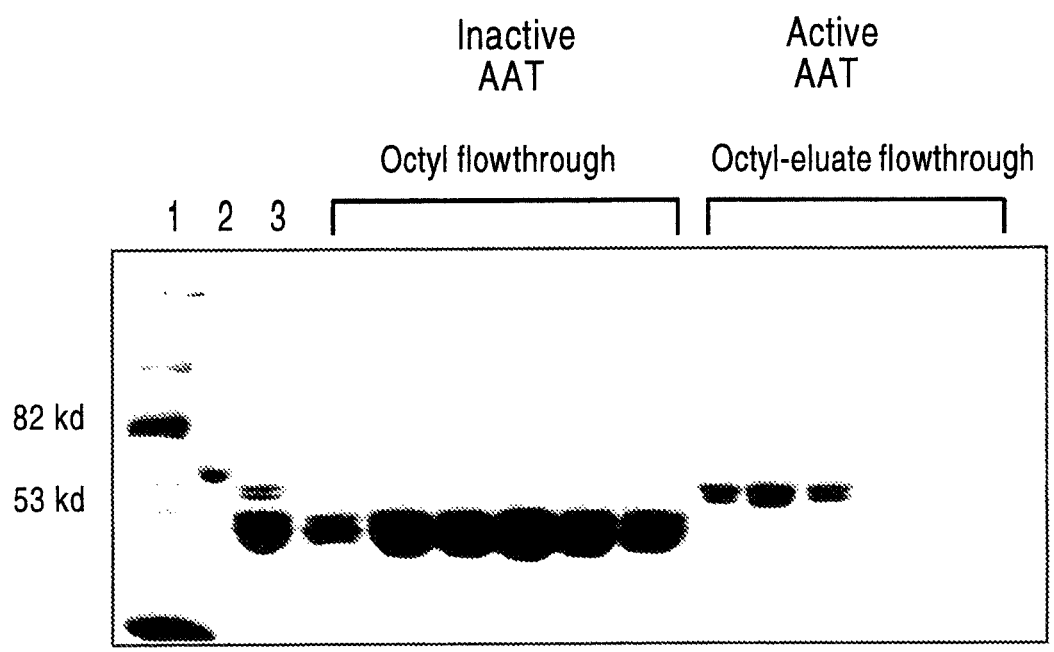

FIG. 8 depicts AAT derived from rice cell extracts purified initially through Con-A and DEAE Sepharose respectively, then loaded onto an octyl Sepharose column. Octyl Sepharose is the final purification step and separates active AAT from an inactivated form of the protein. Lane 1, molecular weight markers; Lane 2, 2 μg purified non-recombinant human AAT as a standard; Lane 3, pooled eluate from the DEAE Sepharose column. The remaining columns show the flow-through and the eluate from the octyl Sepharose column. Approximately 50 μL from each column fraction was loaded onto an SDS-PAGE gel and the proteins visualized by Coomassie staining. Octyl Sepharose flow-through shows the inactive AAT protein while the eluate resolves active AAT.

Figure 1:
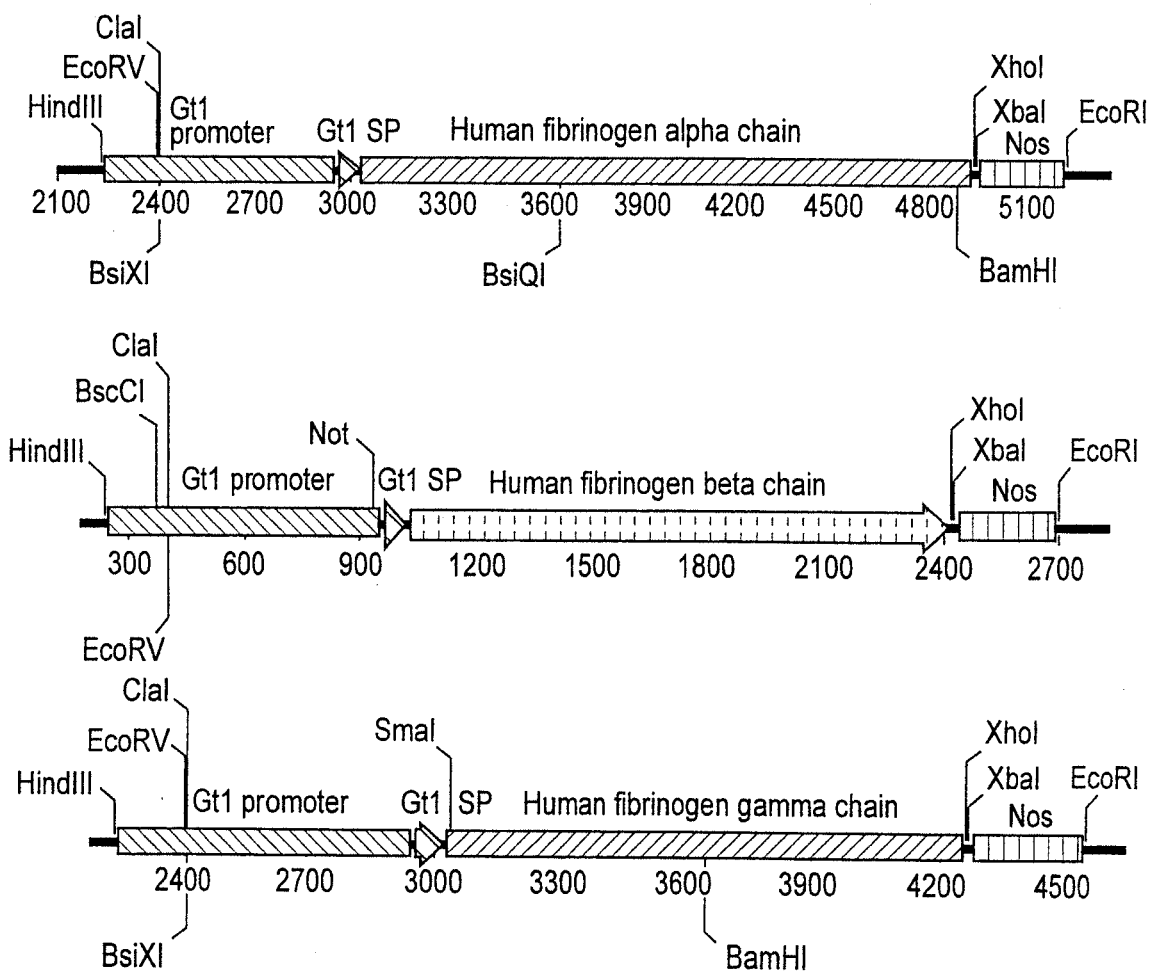
FIG. 1 shows plasmids with constructs containing three codon-optimized genes encoding the fibrinogen polypeptides α (pAPI 398), β (pAP I 417) and γ (pAPI 327) (SEQ ID NO: 1-3), each under the control of the rice glutelin promoter Gt1. These plasmids, including a plasmid (not shown) containing the hygromycin selectable marker, were bombarded into embryogenic rice callus to create transgenic rice plants expressing these three genes in mature rice seeds.
Figure 2:
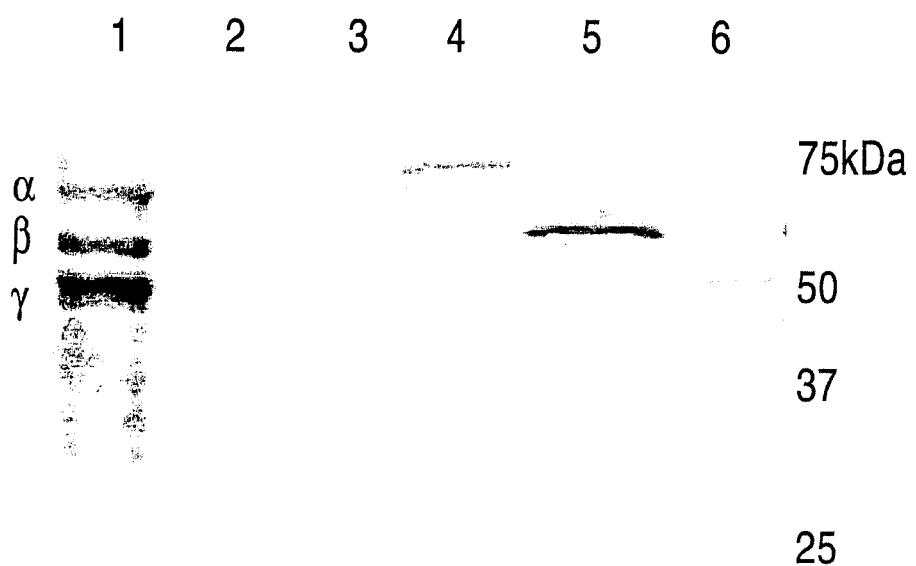
FIG. 2 shows a Western blot analysis of transgenic rice lines expressing individual subunits of human fibrinogen. Lane 1, positive control, purified native human fibrinogen (obtained from the Red Cross) showing all three polypeptide chains; Lane 2, extract from Tapei 309, a non transgenic rice variety; Lane 3, molecular weight standard; Lane 4, rice seed extract expressing fibrinogen a chain; Lane 5, rice seed extract expressing fibrinogen β chain; Lane 6, rice seed extract expressing fibrinogen γ chain. Total protein extract of rice seeds was performed in 2% SDS, 1M urea, 1% βMe and PBS pH 7.4. Fibrinogen polypeptides were detected using antibody recognizing all three chains or individual chains only.
Figure 3:
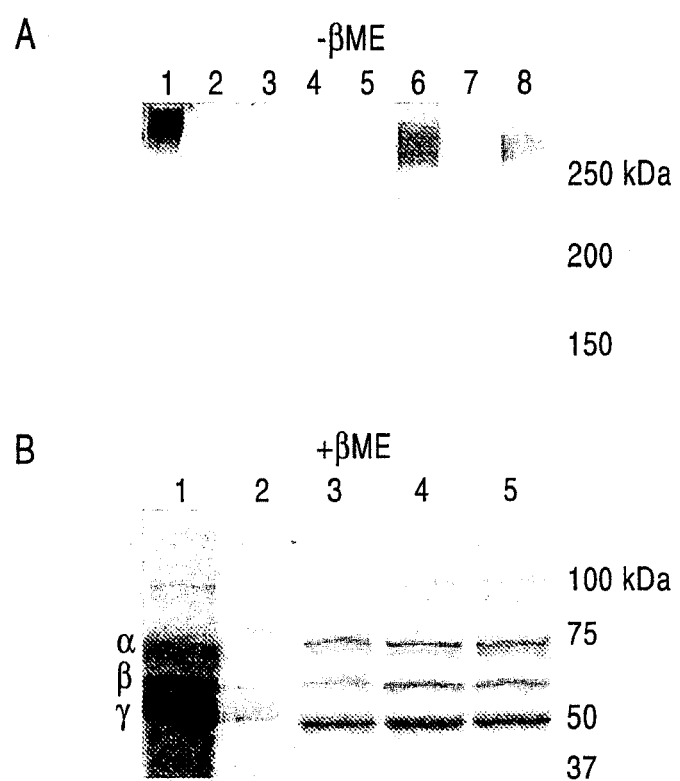
FIG. 3 shows the simultaneous expression of the three fibrinogen polypeptide chains (α, β and γ) in transgenic rice seeds and analyzed via Western blot analysis. Fibrinogen polypeptides and protein aggregates were detected Using antibody recognizing all three chains.
Figure 4:
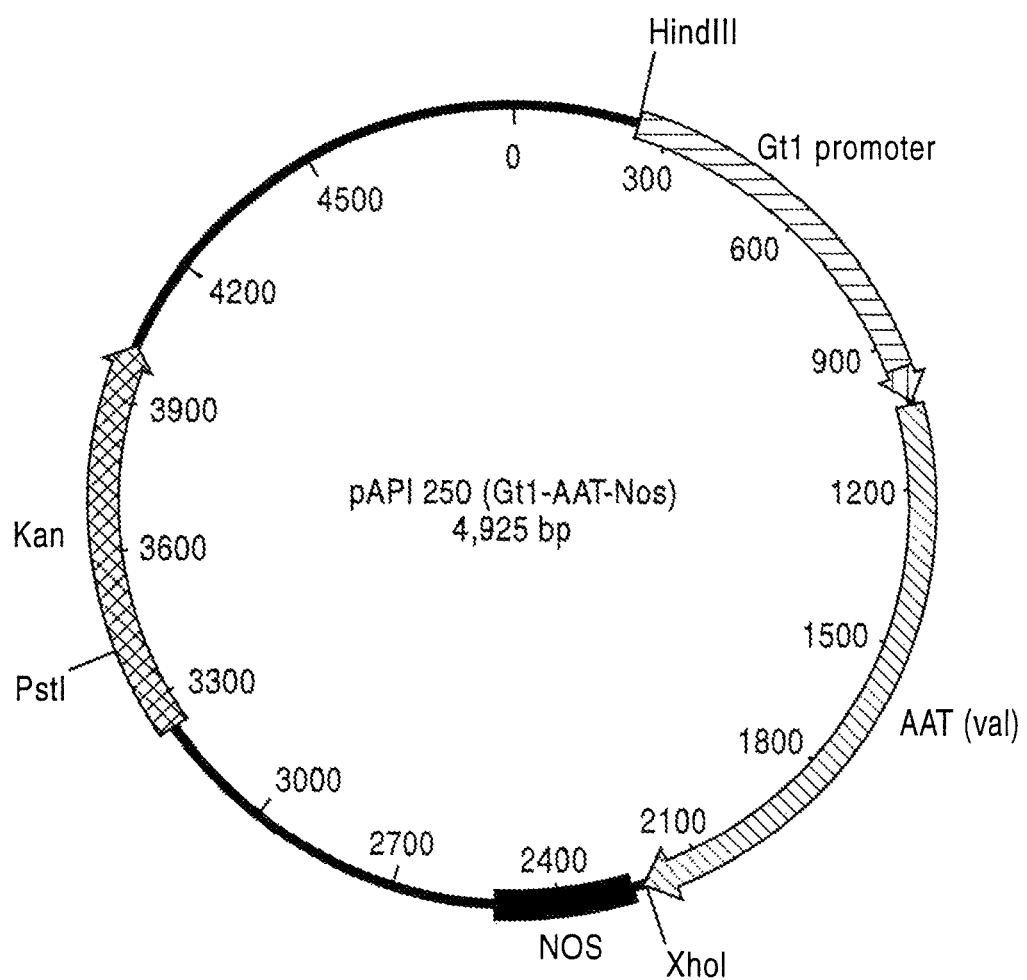
FIG. 4 shows the plasmid pAPI 250 expressing the codon-optimized gene for alpha-1-antitrypsin (AAT) (SEQ ID NO:5) under the control of the rice glutelin promoter Gt1. This plasmid, along with a plasmid (not shown) containing the hygromycin selectable marker gene, was bombarded into embryogenic rice callus to create transgenic rice plants expressing AAT in mature rice seeds.
Figure 5:
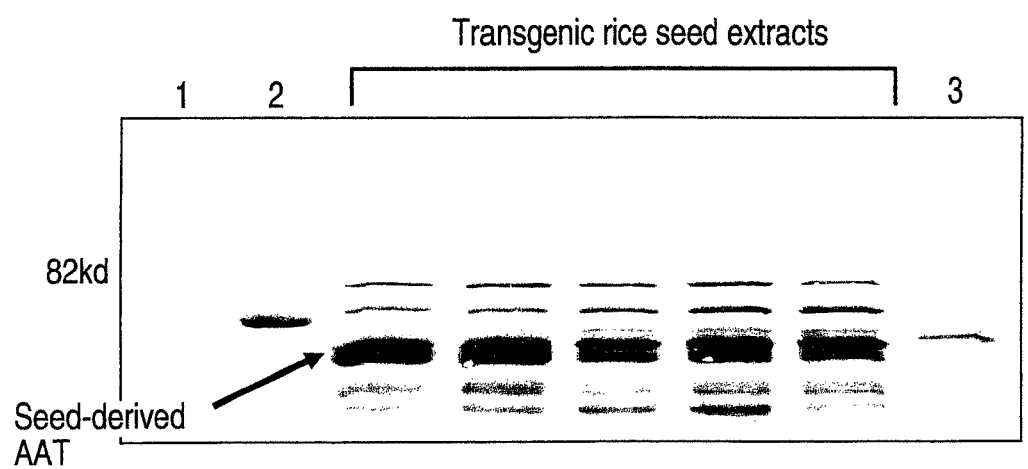
FIG. 5 shows Coomassie brilliant blue staining of aqueous phase extraction of transgenic rice grains expressing human recombinant AAT. Both untransformed (rice var. Kitaake) and transgenic rice seeds (~10 pooled R1 seed from five individual transgenic plants) were ground with PBS pH 7.4 buffer. The resulting extract was spun at 14,000 rpm at 4° C. for 10 min. Supernatant was collected and ~20 μg of this soluble protein extract was resuspended in sample loading buffer, and loaded onto a precast SDS-PAGE gel. Lane 1, molecular weight protein markers; Lane 2, purified non-recombinant human AAT; Lane 3, extract from control non-transformed Kitaake variety. Between lanes 2 and 3, the results from the extracts of the five individual transgenic plants are shown.
Figure 6:
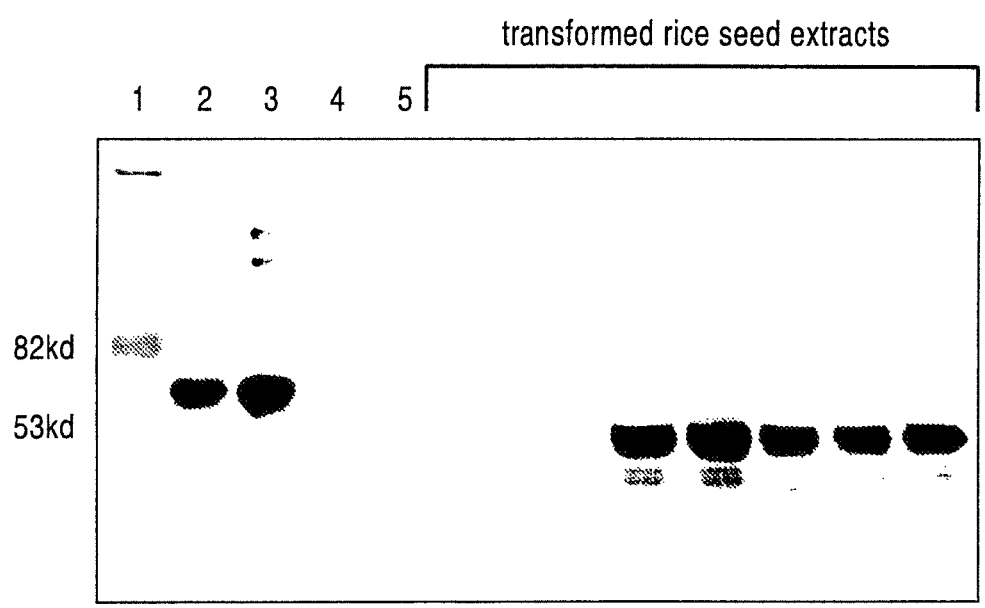
FIG. 6 shows Western blot analysis of recombinant human AA T expressed in transgenic rice grains. The R1 pooled seed soluble protein extracts (~10 μg total protein) from seven independent transgenic rice transformants were prepared as described in FIG. 5 above, separated by SDS-PAGE gel and then blotted onto a nitrocellulose filter. The identification of AAT expressed in rice seeds was carried out by Western analysis using anti-AAT antibody. Lane 1, molecular weight protein markers; Lanes 2 & 3, 1 μg and 2 μg, respectively, of purified nonrecombinant human AAT; Lanes 4 & 5, control, non-transgenic rice extract (var. Kitaake). The final seven lanes show the results from the extracts of the seven individual transgenic plants. Extracts from two of the seven transgenic lines did not express AAT. The shift in gel mobility between the non-recombinant human and recombinant rice-expressed forms is due to the type and glycosylation differences in the human and recombinant rice-expressed proteins.
Figure 7:
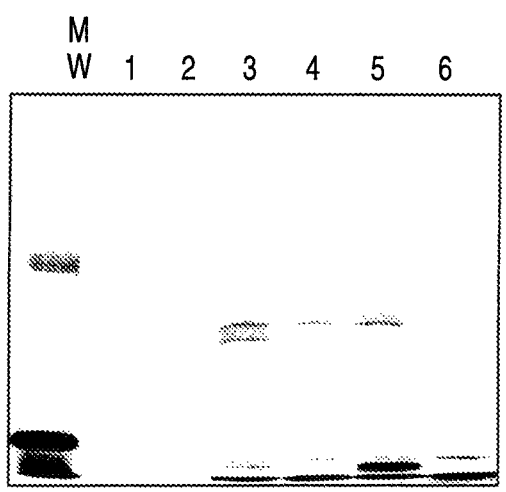
FIG. 7 shows activity of purified recombinant AAT (rAAT) obtained from rice extracts against purified porcine pancreatic elastase (PPE) as determined by Coomassie staining and Western blot analysis. The activity of rAAT is demonstrated by a band shift assay involving the AAT protease substrate, elastase. AAT samples from human and rice extracts were incubated with equal number of moles of PPE at 37° C. for 15 min. Negative control for band shift assay was prepared with the AAT samples incubated with equal volume of PPE added.
Figure 7:
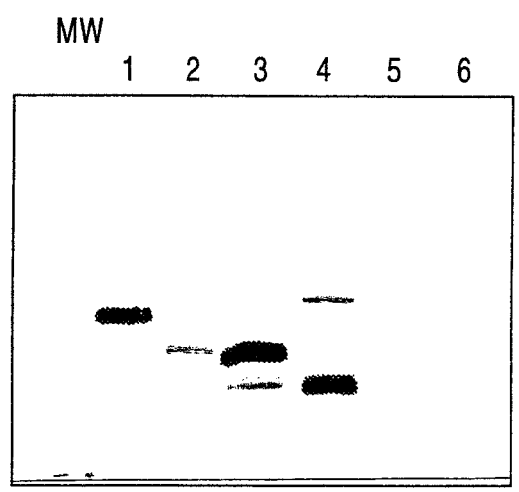
Figure 9:
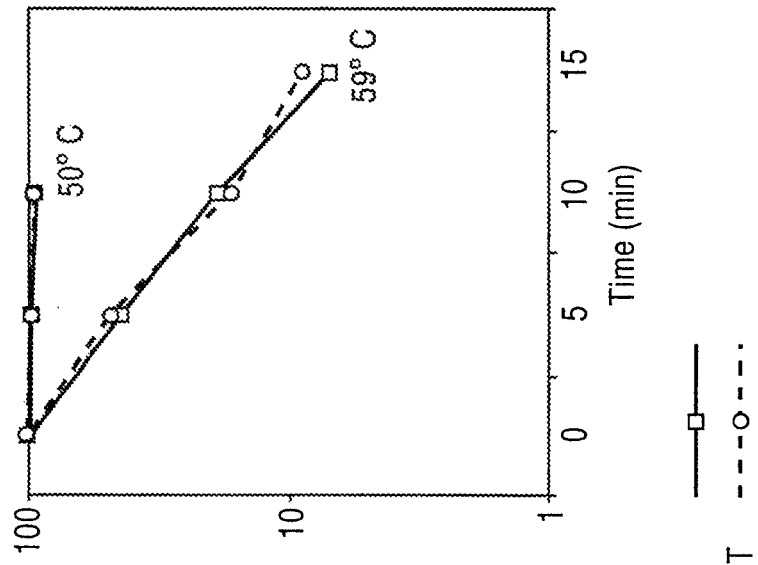
Figure 9:
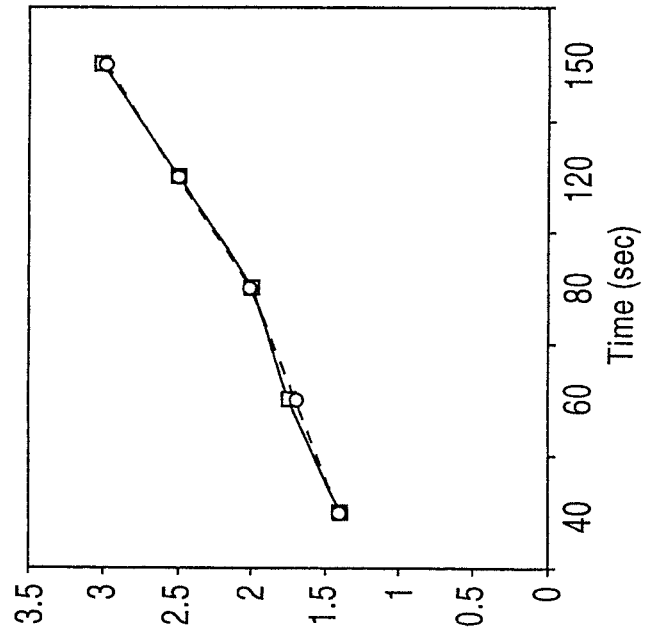

FIG. 9A depicts an AAT association rate constant for activity of purified recombinant AAT against PPE determined (as described by the procedure in FIG. 7) using non-recombinant human AAT as a control. Data were generated by Coomassie protein staining and Western blot analysis, as described in FIG. 7. FIG. 9B depicts the thermostability of plant-derived recombinant AAT versus native human AAT determined by the PPE inhibition assay.

Figure 10:
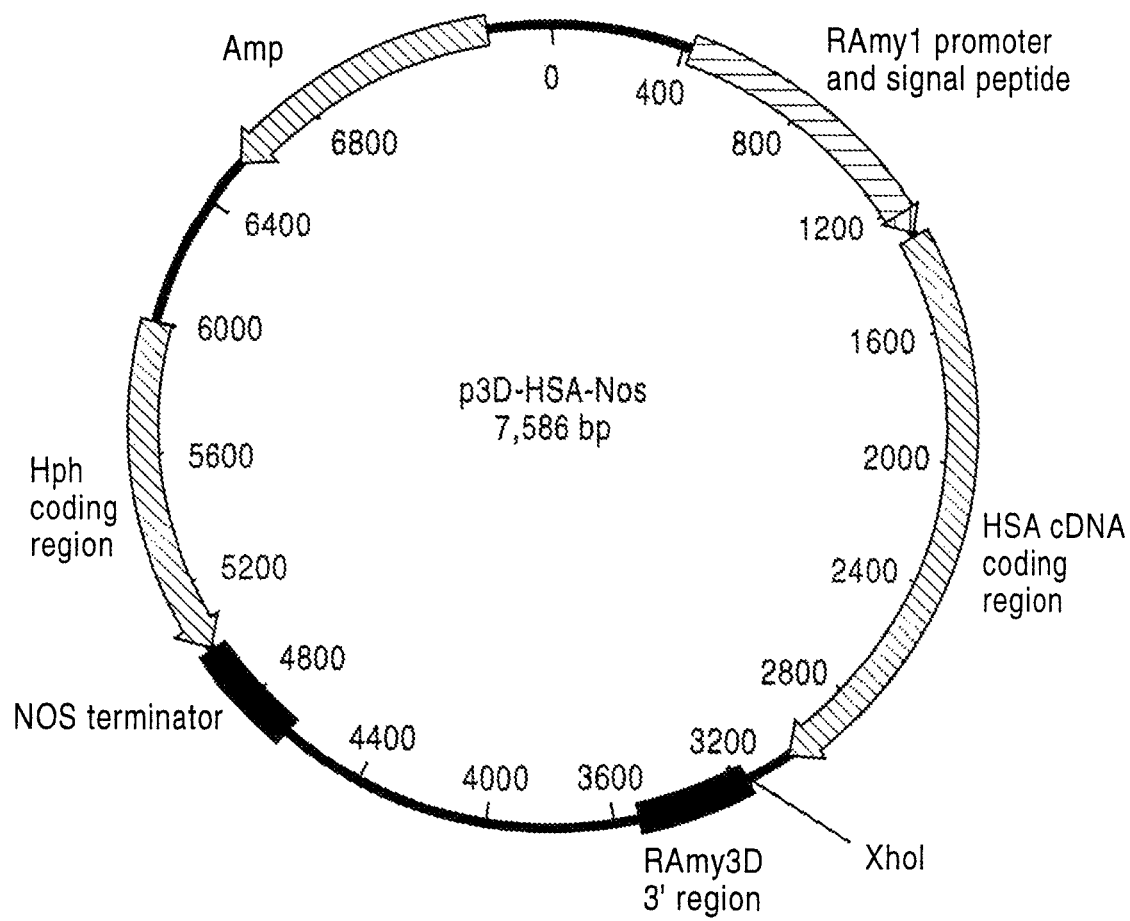

FIG. 10 shows the plasmid pAPI 9 for expression of codon-optimized human serum albumin (HSA) (SEQ ID NO:4) under the control of the rice Amy1A promoter/signal peptide. This plasmid is useful for the expression of HSA in germinated rice seeds.

Figure 11:
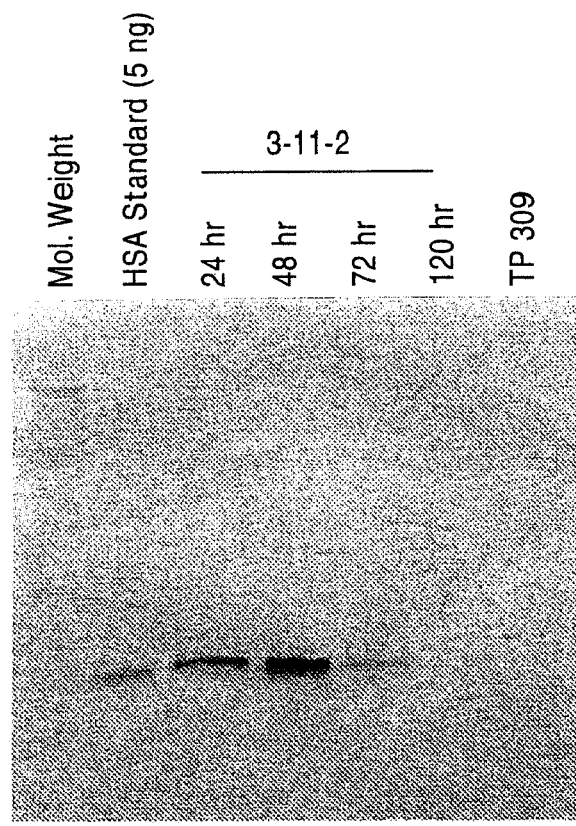

FIG. 11 shows the expression of HSA in transgenic rice seeds. Pooled seed from transgenic rice line 3-11-2 were imbibed in water for 24 hours, then 2 μM gibberelic acid (GA) was added. Seed samples were extracted at 24, 48, 72, and 120 hours post GA addition and soluble proteins were extracted and prepared for Western analysis. 15 μg of soluble protein were loaded onto each lane along with protein isolated from the non-transfromed negative control line TP309. The blot was probed with monoclonal antibody prepared against HSA.

DETAILED DESCRIPTION OF THE INVENTION

Unless otherwise indicated, all terms used herein have the meanings given below or are generally consistent with same meaning that the terms have to those skilled in the art of the present invention. Practitioners are particularly directed to Sam brook et al. (1989) Molecular Cloning: A Laboratory Manual (Second Edition), Cold Spring Harbor Press, Plainview, N.Y., Ausubel F. M. et al., (1993) Current Protocols in Molecular Biology, John Wiley & Sons, New York, N.Y., and Gelvin and Schilperoot, eds. (1997) Plant Molecular Biology Manual, Kluwer Academic Publishers, The Netherlands for definitions and terms of the art.

The polynucleotides of the invention may be in the form of RNA or in the form of DNA, and include messenger RNA, synthetic RNA and DNA, cDNA, and genomic DNA The DNA may be double-stranded or single-stranded, and if single-stranded may be the coding strand or the non-coding (anti-sense, complementary) strand.

The term "stably transformed" with reference to a plant cell means the plant cell has a non-native (heterologous) nucleic acid sequence integrated into its genome which is maintained through two or more generations.

By "host cell" is meant a cell containing a vector and supporting the replication and/or transcription and/or expression of the heterologous nucleic acid sequence. Preferably, according to the invention, the host cell is a monocot plant cell. Other host cells may be used as secondary hosts, including bacterial, yeast, insect, amphibian or mammalian cells, to move DNA to a desired plant host cell.

A "plant cell" refers to any cell derived from a plant, including undifferentiated tissue (e.g., callus) as well as plant seeds, pollen, propagules, embryos, suspension cultures, meristematic regions, leaves, roots, shoots, gametophytes, sporophytes and microspores.

The term "mature plant" refers to a fully differentiated plant.

The term "seed product" includes, but is not limited to, seed fractions such as de-hulled whole seed, flour (seed that has been de-hulled by milling and ground into a powder) a seed extract, preferably a protein extract (where the protein fraction of the flour has been separated from the carbohydrate fraction), malt (including malt extract or malt syrup) and/or a purified protein fraction derived from the transgenic grain.

The term "biological activity" refers to any biological activity typically attributed to that protein by those of skill in the art.

The term "blood protein" refers to one or more proteins, or biologically active fragments thereof, found in normal human blood, including, without limitation, hemoglobin, alpha-1-antitrypsin, fibrinogen, human serum albumin, prothrombin/thrombin, antithrombin III, antibodies, blood coagulation factors (Factor V, Factor VI, Factor VII, Factor VIII, Factor IX, Factor X, Factor XI, Factor XII, Factor XIII, Fletcher Factor, Fitzgerald Factor and von Willebrand Factor), and biologically active fragments thereof.

The term "non-nutritional" refers to a pharmaceutically acceptable excipient which does not as its primary effect provide nutrition to the recipient. Preferably, it may provide one of the following services to an enterically delivered formulation, including acting as a carrier for a therapeutic protein, protecting the protein from acids in the digestive tract, providing a time-release of the active ingredients being delivered, or otherwise providing a useful quality to the formulation in order to administer to the patient the blood proteins.

"Monocot seed components" refers to carbohydrate, protein, and lipid components extractable from monocot seeds, typically mature monocot seeds.

"Seed maturation" refers to the period starting with fertilization in which metabolizable reserves, e.g., sugars, oligosaccharides, starch, phenolics, amino acids, and proteins, are deposited, with and without vacuole targeting, to various tissues in the seed (grain), e.g., endosperm, testa, aleurone layer, and scutellar epithelium, leading to grain enlargement, grain filling, and ending with grain desiccation.

"Maturation-specific protein promoter" refers to a promoter exhibiting substantially upregulated activity (greater than 25%) during seed maturation.

"Heterologous DNA" refers to DNA which has been introduced into plant cells from another source, or which is from a plant source, including the same plant source, but which is under the control of a promoter that does not normally regulate expression of the heterologous DNA.

"Heterologous protein" is a protein encoded by a heterologous DNA.

A "signal sequence" is an N- or C-terminal polypeptide sequence which is effective to localize the peptide or protein to which it is attached to a selected intracellular or extracellular region. Preferably, according to the invention, the signal sequence targets the attached peptide or protein to a location such as an endosperm cell, more preferably an endosperm-cell organelle, such as an intracellular vacuole or other protein storage body, chloroplast, mitochondria, or endoplasmic reticulum, or extracellular space, following secretion from the host cell.

Expression vectors for use in the present invention are chimeric nucleic acid constructs (or expression vectors or cassettes), designed for operation in plants, with associated upstream and downstream sequences.

In general, expression vectors for use in practicing the invention include the following operably linked components that constitute a chimeric gene: a promoter from the gene of a maturation-specific monocot plant storage protein, a first DNA sequence, operably linked to the promoter, encoding a monocot plant seed-specific signal sequence (such as an N-terminal leader sequence or a C-terminal trailer sequence) capable of targeting a polypeptide linked thereto to an endosperm cell, preferably an endosperm-cell organelle, such as a protein storage body, and a second DNA sequence, linked in translation frame with the first DNA sequence, encoding a human blood protein. The Signal sequence is preferably cleaved from the human blood protein in the plant cell.

The chimeric gene, in turn, is typically placed in a suitable plant-transformation vector having (i) companion sequences upstream and/or downstream of the chimeric gene which are of plasmid or viral origin and provide necessary characteristics to the vector to permit the vector to move DNA from bacteria to the desired plant host; (ii) a selectable marker sequence; and (iii) a transcriptional termination region generally at the opposite end of the vector from the transcription initiation regulatory region.

Numerous types of appropriate expression vectors, and suitable regulatory sequences are known in the art for a variety of plant host cells. The promoter region is chosen to be regulated in a manner allowing for induction under seed-maturation conditions. In one aspect of this embodiment of the invention, the expression construct includes a promoter which exhibits specifically upregulated activity during seed maturation. Promoters for use in the invention are typically derived from cereals such as rice, barley, wheat, oat, rye, corn, millet, triticale or sorghum. Examples of such promoters include the maturation-specific promoter region associated with one of the following maturation-specific monocot plant storage proteins: rice glutelins, oryzins, and prolamines, barley hordeins, wheat gliadins and glutelins, maize zeins and glutelins, oat glutelins, and sorghum kafirins, millet pennisetins, and rye secalins. Exemplary regulatory regions from these genes are exemplified by SEQ ID NOS:6-14. Other promoters suitable for expression in maturing seeds include the barley endosperm-specific B1-hordein promoter, GluB-2 promoter, Bx7 promoter, Gt3 promoter, GluB-1 promoter and Rp-6 promoter, particularly if these promoters are used in conjunction with transcription factors.

Of particular interest is the expression of the nucleic acid encoding a human blood protein from a promoter that is preferentially expressed in plant seed tissue. Examples of such promoter sequences include those sequences derived from sequences encoding plant storage protein genes or from genes involved in fatty acid biosynthesis in oilseeds. Exemplary preferred promoters include a glutelin (Gt1) promoter, as exemplified by SEQ ID NO:6, which effects gene expression in the outer layer of the endosperm, and a globulin (Glb) promoter, as exemplified by SEQ ID NO:7, which effects gene expression in the center of the endosperm. Promoter sequences for regulating transcription of gene coding sequences operably linked thereto include naturally-occurring promoters, or regions thereof capable of directing seed-specific transcription, and hybrid promoters, which combine elements of more than one promoter. Methods for construction such hybrid promoters are well known in the art.

In some cases, the promoter is native to the same plant species as the plant cells into which the chimeric nucleic acid construct is to be introduced. In other embodiments, the promoter is heterologous to the plant host cell.

Alternatively, a seed-specific promoter from one type of monocot may be used regulate transcription of a nucleic acid coding sequence from a different monocot or a non-cereal monocot.

In addition to encoding the protein of interest, the expression cassette or heterologous nucleic acid construct includes DNA encoding a signal peptide that allows processing and translocation of the protein, as appropriate. Exemplary signal sequences are those sequences associated with the monocot maturation-specific genes: glutelins, prolamines, hordeins, gliadins, glutenins, zeins, albumin, globulin, AOP glucose pyrophosphorylase, starch synthase, branching enzyme, Em, and lea. Exemplary sequences encoding a signal peptide for a protein storage body are identified herein as SEQ ID NOS: 15-21.

In one preferred embodiment, the method is directed toward the localization of proteins in an endosperm cell, preferably an endosperm-cell organelle, such as a protein storage body, mitochondrion, endoplasmic reticulum, vacuole, chloroplast or other plastidic compartment. For example, when proteins are targeted to plastids, such as chloroplasts, in order for expression to take place the construct also employs the use of sequences to direct the gene product to the plastid. Such sequences are referred to herein as chloroplast transit peptides (CTP) or plastid transit peptides (PTP). In this manner, when the gene of interest is not directly inserted into the plastid, the expression construct additionally contains a gene encoding a transit peptide to direct the gene of interest to the plastid. The chloroplast transit peptides may be derived from the gene of interest, or may be derived from a heterologous sequence having a CTP. Such transit peptides are known in the art. See, for example, (Smeekens et al., 1986; Wasmann et al., 1986; Von Heijne et at, 1991, U.S. Pat. Nos. 4,940,835 and 5,728,925. Additional transit peptides for the translocation of the protein to the endoplasmiC reticulum (ER) (Chrispeels, 1991; Vitale and Chrispeels, 1992), nuclear localization signals (Shieh et al., 1993; Varagona et al., 1992) or vacuole (Raikhel and Chrispeels 1992; Bednarek and Raikel, 1992; also see U.S. Pat. No. 5,360,726) may also find use in the constructs of the present invention.

Another exemplary class of signal sequences are sequences effective to promote secretion of heterologous protein from aleurone cells during seed germination, including the signal sequences associated with alpha-amylase, protease, carboxypeptidase, endoprotease, ribonuclease, DNase/RNase, (1-3)-betaglucanase, (1-3)(1-4)-beta-glucanase, esterase, acid phosphatase, pentosamine, endoxylanase, β-xylopyranosidase, arabinofuranosidase, beta-glucosidase, (1-6)-beta-glucanase, perioxidase, and lysophospholipase.

Since many protein storage proteins are under the control of a maturation-specific promoter, and this promoter is operably linked to a signal sequence for targeting to a protein body, the promoter and signal sequence can be isolated from a single protein-storage gene, then operably linked to a blood protein in the chimeric gene construction. One preferred and exemplary promoter-signal sequence is from the rice Gt1 gene, having an exemplary sequence identified by SEQ ID NO:6. Alternatively, the promoter and leader sequence may be derived from different genes. One preferred and exemplary promoter-signal sequence combination is the rice Glb promoter linked to the rice Gt1 leader sequence, as exemplified by SEQ ID NO:7.

Preferably, expression vectors or heterologous nucleic acid constructs designed for operation in plants comprise companion sequences upstream and downstream to the expression cassette. The companion sequences are of plasmid or viral origin and provide necessary characteristics to the vector to permit the vector to move DNA from a secondary host to the plant host, such as, sequences containing an origin of replication and a selectable marker. Typical secondary hosts include bacteria and yeast.

In one embodiment, the secondary host is E. coli, the origin of replication is a ColE1-type, and the selectable marker is a gene encoding ampicillin resistance. Such sequences are well known in the art and are commercially available as well (e.g., Clontech, Palo Alto, Calif.; Stratagene, La Jolla, Calif.

The transcription termination region may be taken from a gene where it is normally associated with the transcriptional initiation region or may be taken from a different gene. Exemplary transcriptional termination regions include the NOS terminator from Agrobacterium Ti plasmid and the rice α-amylase terminator.

Polyadenylation tails may also be added to the expression cassette to optimize high levels of transcription and proper transcription termination, respectively. Polyadenylation sequences include, but are not limited to, the Agrobacterium octopine synthetase signal, or the nopaline synthase of the same species.

Suitable selectable markers for selection in plant cells include, but are not limited to, antibiotic resistance genes, such as, kanamycin (nptll), G418, bleomycin, hygromycin, chloramphenicol, ampicillin, tetracycline, and the like. Additional selectable markers include a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulphonylurea resistance; and a methotrexate resistant DHFR gene.

The particular marker gene employed is one which allows for selection of transformed cells as compared to cells lacking the DNA which has been introduced. Preferably, the selectable marker gene is one which facilitates selection at the tissue culture stage, e.g., a kanamyacin, hygromycin or ampicillin resistance gene.

The vectors of the present invention may also be modified to include intermediate plant transformation plasmids that contain a region of homology to an Agrobacterium tumefaciens vector, a T-DNA border region from Agrobacterium tumefaciens, and chimeric genes or expression cassettes (described above). Further, the vectors of the invention may comprise a disarmed plant tumor inducing plasmid of Agrobacterium tumefaciens.

In general, a selected nucleic acid sequence is inserted into an appropriate restriction endonuclease site or sites in the vector. Standard methods for cutting, ligating and transformation into a secondary host cell, known to those of skill in the art, are used in constructing vectors for use in the present invention. (See generally, Maniatis et al., Ausubel et al., and Gelvin et al., supra.)

Plant cells or tissues are transformed with expression constructs (heterologous nucleic acid constructs, e.g., plasmid DNA into which the gene of interest has been inserted) using a variety of standard techniques. Effective introduction of vectors in order to facilitate enhanced plant gene expression is an important aspect of the invention. It is preferred that the vector sequences be stably transformed, preferably integrated into the host genome.

The method used for transformation of host plant cells is not critical to the present invention. The skilled artisan will recognize that a wide variety of transformation techniques exist in the art, and new techniques are continually becoming available. Any technique that is suitable for the target host plant may be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to calcium-phosphate-DNA co-precipitation, electroporation, microinjection, Agrobacterium-mediated transformation, liposome-mediated transformation, protoplast fusion or microprojectile bombardment (Christou, 1992; Sanford et al., 1993). The skilled artisan can refer to the literature for details and select suitable techniques for use in the methods of the present invention.

When Agrobacterium is used for plant cell transformation, a vector is introduced into the Agrobacterium host for homologous recombination with T-DNA or the Ti-or Ri-plasmid present in the Agrobacterium host The Ti-or Ri-plasmid containing the T-DNA for recombination may be armed (capable of causing gall formation) or disarmed (incapable of causing gall formation), the latter being permissible, so long as the vir genes are present in the transformed Agrobacterium host The armed plasmid can give a mixture of normal plant cells and gall.

In some instances where Agrobacterium is used as the vehicle for transforming host plant cells, the expression or transcription construct bordered by the T-DNA border region(s) is inserted into a broad host range vector capable of replication in E. coli and Agrobacterium, examples of which are described in the literature, for example pRK2 or derivatives thereof. See, for example, Ditta et al., 1980 and EPA 0 120 515. Alternatively, one may insert the sequences to be expressed in plant cells into a vector containing separate replication sequences, one of which stabilizes the vector in E. coli, and the other in Agrobacterium. See, for example, McBride and Summerfeit 1990, wherein the pRiHRI (Jouanin, et al., 1985), origin of replication is utilized and provides for added stability of the plant expression vectors in host Agrobacterium cells.

Included with the expression construct and the T-DNA is one or more selectable marker coding sequences which allow for selection of transformed Agrobacterium and transformed plant cells. A number of antibiotic resistance markers have been developed for use with plant cells, these include genes inactivating antibiotics such as kanamycin, the aminoglycoside G418, hygromycin, or the like. The particular marker employed is not essential to this invention, with a particular marker preferred depending on the particular host and the manner of construction.

For Agrobacterium-mediated transformation of plant cells, explants are incubated with Agrobacterium for a time sufficient to result in infection, the bacteria killed, and the plant cells cultured in an appropriate selection medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of the recombinant protein produced by the plants.

There are a number of possible ways to obtain plant cells containing more than one expression construct In one approach, plant cells are co-transformed with a first and second construct by inclusion of both expression constructs in a single transformation vector or by using separate vectors, one of which expresses desired genes. The second construct can be introduced into a plant that has already been transformed with the first expression construct, or alternatively, transformed plants, one having the first construct and one having the second construct, can be crossed to bring the constructs together in the same plant.

In a preferred embodiment, the plants used in the methods of the present invention are derived from members of the taxonomic family known as the Gramineae. This includes all members of the grass family of which the edible varieties are known as cereals. The cereals include a wide variety of species such as wheat (*Triticum* sps.), rice (*Oryza* sps.) barley (*Hordeum* sps.) oats, (*Avena* sps.) rye (*Secale* sps.), corn (maize) (*Zea* sps.) and millet (*Pennisettum* sps.). In practicing the present invention, preferred grains are rice, wheat, maize, barley, rye and triticale, and most preferred is rice.

In order to produce transgenic plants that express human blood protein in seeds, monocot plant cells or tissues derived from them are transformed with an expression vector comprising the coding sequence for a human blood protein. The transgenic plant cells are cultured in medium containing the appropriate selection agent to identify and select for plant cells which express the heterologous nucleic acid sequence. After plant cells that express the heterologous nucleic acid sequence are selected, whole plants are regenerated from the selected transgenic plant cells. Techniques for regenerating whole plants from transformed plant cells are generally known in the art Transgenic plant lines, e.g., rice, wheat, corn or barely, can be developed and genetic crosses carried out using conventional plant breeding techniques.

Transformed plant cells are screened for the ability to be cultured in selective media having a threshold concentration of a selective agent Plant cells that grow on or in the selective media are typically transferred to a fresh supply of the same media and cultured again. The explants are then cultured under regeneration conditions to produce regenerated plant shoots. After shoots form, the shoots are transferred to a selective rooting medium to provide a complete plantlet. The plantlet may then be grown to provide seed, cuttings, or the like for propagating the transformed plants. The method provides for efficient transformation of plant cells and regeneration of transgenic plants, which can produce a recombinant human blood protein.

The expression of the recombinant human blood protein may be confirmed using standard analytical techniques such as Western blot, ELISA, PCR, HPLC, NMR, or mass spectroscopy, together with assays for a biological activity specific to the particular protein being expressed.

A purified blood protein recombinantly produced in a plant cell, preferably substantially free of contaminants of the host plant cell, and preferably comprising at least one plant glycosyl group is also provided by the invention. The plant glycosyl groups, while identifying that the blood protein was produced in a plant, does not significantly impair the biological activity of the blood protein in any of the applied therapeutic contexts (preferably less than 25% loss of activity, more preferably less than 10% loss of activity, as compared to a corresponding non-recombinant human blood protein). Typically, in accordance with some embodiments of the invention, the human blood protein constitutes at least about 0.5%, at least about 1.0% or at least about 2.0% of the total soluble protein in the seeds harvested from the transgenic plant. In a preferred embodiment, however, protein expression is much higher than previously reported, i.e., at least about 3.0%, which makes commercial production quite feasible. Advantageously, protein expression is at least about 5.0%, at least about 10%, at least about 15%, at least about 20%, at least about 30%, or even at least about 40% of total soluble protein.

The invention includes plant seed product prepared from the harvested seeds. Preferably, the human blood protein constitutes at least about 3.0% of the total soluble protein in the seed product, more preferably at least about 5.0%, and most preferably at least about 10.0%. As shown in the figures, the expression of human blood proteins in rice grains, represented by AAT, the three fibrinogen polypeptides and HSA represent at least about 10% of total soluble protein.

The present invention also provides compositions comprising human blood proteins produced recombinantly in the seeds of monocot plants, and methods of making such compositions. In practicing the invention, a human blood protein is produced in the seeds or grain of transgenic plants that express the nucleic acid coding sequence for the human blood protein. After expression, the blood protein may be provided to a patient in substantially unpurified form (Le., at least 20% of the composition comprises plant material), or the blood protein may be isolated or purified from a product of the mature seed (e.g., flour, extract, malt or whole seed, etc.) and formulated for delivery to a patient.

Such compositions can comprise a formulation for the type of delivery intended. Delivery types can include, e.g. parenteral, enteric, inhalation, intranasal or topical delivery. Parenteral delivery can include, e.g. intravenous, intramuscular, or suppository. Enteric delivery can include, e.g. oral administration of a pill, capsule, or other formulation made with a non-nutritional pharmaceutically acceptable excipient, or a composition with a nutrient from the transgenic plant, for example, in the grain extract in which the protein is made, or from a source other than the transgenic plant Such nutrients include, for example, salts, saccharides, vitamins, minerals, amino acids, peptides, and proteins other than the human blood protein. Intranasal and inhalant delivery systems can include spray or aerosol in the nostrils or mouth. Topical delivery can include, e.g. creams, topical sprays, or salves. Preferably, the composition is substantially free of contaminants of the transgenic plant, preferably containing less than 20% plant material, more preferably less than 10%, and most preferably, less than 5%. The preferable route of administration is enteric, and preferably the composition is non-nutritional.

The blood protein can be purified from the seed product by a mode including grinding, filtration, heat, pressure, salt extraction, evaporation, or chromatography.

The human blood proteins produced in accordance with the invention also include all variants thereof, whether allelic variants or synthetic variants. A "variant" human blood protein-encoding nucleic acid sequence may encode a variant human blood protein amino acid sequence that is altered by one or more amino acids from the native blood protein sequence, preferably at least one amino acid substitution, deletion or insertion. The nucleic acid substitution, insertion or deletion leading to the variant may occur at any residue within the sequence, as long as the encoded amino acid sequence maintains substantially the same biological activity of the native human blood protein. In another embodiment, the variant human blood protein nucleic acid sequence may encode the same polypeptide as the native sequence but, due to the degeneracy of the genetic code, the variant has a nucleic acid sequence altered by one or more bases from the native polynucleotide sequence.

The variant nucleic acid sequence may encode a variant amino acid sequence that contains a "conservative" substitution, wherein the substituted amino acid has structural or chemical properties similar to the amino acid which it replaces and physicochemical amino acid side chain properties and high substitution frequencies in homologous proteins found in nature (as determined, e.g., by a standard Dayhoff frequency exchange matrix or BLOSUM matrix). In addition, or alternatively, the variant nucleic acid sequence may encode a variant amino acid sequence containing a "non-conservative" substitution, wherein the substituted amino acid has dissimilar structural or chemical properties to the amino acid it replaces. Standard substitution classes include six classes of amino acids based on common side chain properties and highest frequency of substitution in homologous proteins in nature, as is generally known to those of skill in the art and may be employed to develop variant human blood protein-encoding nucleic acid sequences.

As will be understood by those of skill in the art, in some cases it may be advantageous to use a human blood protein-encoding nucleotide sequences possessing non-naturally occurring codons. Codons preferred by a particular eukaryotic host can be selected, for example, to increase the rate of human blood protein expression or to produce recombinant RNA transcripts having desirable properties, such as a longer half-life, than transcripts produced from naturally occurring sequence. As an example, it has been shown that codons for genes expressed in rice are rich in guanine (G) or cytosine (C) in the third codon position (Huang et al., 1990). Changing low G+C content to a high G+C content has been found to increase the expression levels of foreign protein genes in barley grains (Horvath et al., 2000). The blood protein encoding genes employed in the present invention were synthesized by Operon Technologies (Alameda, C A based on the rice gene codon bias (Huang et al., 1990) along with the appropriate restriction sites for gene cloning. These 'codon-optimized' genes were linked to regulatory/secretion sequences for seed-directed monocot expression and these chimeric genes then inserted into the appropriate plant transformation vectors.

A human blood protein-encoding nucleotide sequence may be engineered in order to alter the human blood protein coding sequence for a variety of reasons, including but not limited to, alterations which modify the cloning, processing and/or expression of the human blood protein by a cell.

Heterologous nucleic acid constructs may include the coding sequence for a given human blood protein (i) in isolation; (ii) in combination with additional coding sequences; such as fusion protein or signal peptide, in which the human blood protein coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the human blood protein coding sequence is a heterologous gene.

Depending upon the intended use, an expression construct may contain the nucleic acid sequence encoding the entire human blood protein, or a portion thereof. For example, where human blood protein sequences are used in constructs for use as a probe, it may be advantageous to prepare constructs containing only a particular portion of the human blood protein encoding sequence, for example a sequence which is discovered to encode a highly conserved human blood protein region.

The invention provides, in one embodiment, a seed composition containing a flour, extract, or malt obtained from mature monocot seeds and one or more seed produced human blood proteins in unpurified form. Isolating the blood proteins from the flour can entail forming an extract composition by milling seeds to form a flour, extracting the flour with an aqueous buffered solution, and optionally, further treating the extract to partially concentrate the extract and/or remove unwanted components. In a preferred method, mature monocot seeds, such as rice seeds, are milled to a flour, and the flour then suspended in saline or in a buffer, such as Phosphate Buffered Saline ("PBS"), ammonium bicarbonate buffer, ammonium acetate buffer or Tris buffer. A volatile buffer or salt, such as ammonium bicarbonate or ammonium acetate may obviate the need for a salt-removing step, and thus simplify the extract processing method.

The flour suspension is incubated with shaking for a period typically between 30 minutes and 4 hours, at a temperature between 20-55° C., The resulting homogenate is clarified either by filtration or centrifugation. The clarified filtrate or supernatant may be further processed, for example by ultra-filtration or dialysis or both to remove contaminants such as lipids, sugars and salt. Finally, the material maybe dried, e.g., by lyophilization, to form a dry cake or powder. The extract combines advantages of high blood-protein yields, essentially limiting losses associated with protein purification, In general, the protein once produced in a product of a mature seed can be further purified by standard methods known in the art, such as by filtration, affinity column, gel electrophoresis, and other such standard procedures. The purified protein can then be formulated as desired for delivery to a human patient More than one protein can be combined for the therapeutic formulation. The protein may be purified and used in biomedical applications requiring a non-food administration of the protein, The following examples illustrate but are not intended in any way to limit the invention.

EXAMPLE 1

Production of Transgenic Rice Encoding AAT and Fibrinogen Polypeptides

The basic procedures of particle bombardment-mediated rice transformation and plant regeneration were carried out as described by Huang et al., 2001, Rice variety TP309 seeds were dehusked, sterilized in 50% (v/v) commercial bleach for 25 min. and washed with sterile water. The sterilized seeds were placed on rice callus induction medium (RCI) plates containing [N6 salts (Sigma), B5 vitamins (Sigma), 2 mg/l 2,4-D and 3% sucrose], The rice seeds were incubated for 10 days to induce callus formation. Primary callus was dissected from the seeds and placed on RCI for 3 weeks. This was done twice more to generate secondary and tertiary callus which was used for bombardment and continued subculture, A callus of 1-4 mm diameter was placed in a 4 cm circle on RCI with 0.3M mannitol 0.3M sorbitol for 5-24 hrs prior to bombardment. Microprojectile bombardment was carried out using the Biolistic PDC-1000/He system (Bio-Rad). The procedure requires 1.5 mg gold particles (60 µg/ml) coated with 2.5 µg DNA. DNA-coated gold particles were bombarded into rice calli with a He pressure of 1100psi. After bombardment, the callus was allowed to recover for 48 hrs. and then transferred to RCI with 30 mg/l hygromycin B for selection and incubated in the dark for 45 days at 26° C. Transformed calli were selected and transferred to RCI (minus 2,4-D) containing 5 mg/l ABA, 2 mg/l BAP, 1 mg/l NAA and 30mg/l hygromycin B for 9-12 days. Transformed calli were transferred to regeneration medium consisting of RCI (minus 2,4-D), 3 mg/l BAP, and 0.5 mg/l NAA without hygromycin B and cultured under continuous lighting conditions from 2-4 weeks. Regenerated plantlets (1-3 cm high) were transferred to rooting medium whose concentration was half that of MS medium (Sigma) plus 1% sucrose and 0.05 mg/l NAA. After 2 weeks on rooting medium, the plantlets developed roots and the shoots grew to about 10 cm. The plants were transferred to a 6.5×6.5 cm pots containing a mix of 50% commercial soil (Sunshine #1) and 50% soil from rice fields. The plants were covered by a plastic container to maintain nearly 100% humidity and grown under continuous light for 1 week. The transparent plastic cover was slowly shifted over a 1 day period to gradually reduce humidity and water and fertilizers added as necessary. When the transgenic RO plants were approximately 20 cm in height, they were transferred to a greenhouse where they grew to maturity.

Individual R1 seed grains from the individual R0 regenerated plants were dissected into embryos and endosperms. Expression levels of recombinant blood proteins (AAT and fibrinogen polypeptides) in the isolated rice endosperms were determined. Embryos from the individual R1 grains with high recombinant protein expression were sterilized in 50% bleach for 25 min and washed with sterile distilled water. Sterilized embryos were placed in a tissue culture tube containing ½ MS basal salts with the addition of 1% sucrose and 0.05 mg/l NAA. Embryos were germinated and plantlets having ~7 cm shoots and healthy root systems were obtained in about 2 weeks. Mature R1 plants were obtained as regenerants.

EXAMPLE 2

Production of Rice Extract Containing Recombinant Blood Proteins and its Use in Parenteral and Enteric Formulations
General Procedure for Production of Rice Extract Transgenic rice containing heterologous polypeptides can be converted to rice extracts by either a dry milling or wet milling process. In the dry milling process, transgenic paddy rice seeds containing the heterologous polypeptides were dehusked with a dehusker. The rice was grounded into a fine flour though a dry milling process, for example, in one experiment, at speed 3 of a model 91 Kitchen Mill from K-TEC. Phosphate buffered saline ("PBS"), containing 0.135 N NaCl, 2.7 mM KCl, 10 mM $Na_2HPO_4$, 1.7 mM $KH_2PO_4$, at pH 7.4, with or without additional NaCl, such as 0.35 N NaCl, was added to the rice flour. In some experiments, approximately 10 ml of extraction buffer was used for each 1 g of flour. In other experiments, the initial flour/buffer ratio varied over a range such as 1 g/40 ml to 1 g/10 ml. The mixture was incubated at room temperature with gentle shaking for 1 hr. In other experiments, the incubation temperature was lower or higher, such as from about 22° C. to about 60° C., and the incubation time was longer or shorter, such as from about 10 minutes to about 24 hours. A Thermolyne VariMix platform mixer set at high speed was used to keep the particulates suspended.

In place of PBS, other buffers such as ammonium bicarbonate, were used in some experiments. In one embodiment, 10 liters of 0.5M ammonium bicarbonate was added to 1 kg of rice flour.

The resulting homogenate was clarified either by filtration or centrifugation. For the filtration method, the mixture was allowed to settle for about 30 minutes at room temperature, after which the homogenate was collected and filtered. Filters in three different configurations were purchased from Pall Gemansciences and used. They were: a 3 μm pleated capsule, a 1.2 μm serum capsule and a Suporcap capsule 50 (0.2 μm). For centrifugation, a Beckman J2-HC centrifuge was used and the mixture was centrifuged at 30,000 g at 4° C. for about 1 hour. The supernatant was retained and the pellet discarded.

In one embodiment, the filtrate and supernatant were further processed, for example by ultra-filtration or dialysis or both to remove components such as lipids, sugars and salt.

The filtrate from the above filtration procedure, which is also called the clarified extract, was then concentrated using a spiral wound tangential flow filter operated in a batch recirculation mode. In one embodiment, PES (polyethersulfone) 3000-4000 molecular weight cutoff membranes were used for this step. These final concentrated extracts were held overnight in a cold room.

The concentrated extracts were next dried to a powder by lyophilization. The lyophilized material was scraped from the lyophilizer trays and combined into a plastic bag. The dry material was compressed by drawing a vacuum on the bag and then the material was blended and the particle size reduced by hand-kneading it through the plastic.

Rice extract can also be produced using a wet milling procedure. Transgenic paddy rice seeds containing recombinant human blood protein can be rehydrated for a period of 0 to 288 hrs at 30° C. The rehydrated seeds are ground in PBS extraction buffer. The initial seed/buffer ratio can vary over a range such as 1 g/40 ml to 1 g/10 ml.

Over 20% human blood protein can be recovered from the wet milling process. The result of the wet milling becomes an initial extract that may be kept cold (4° C.) or stored frozen until use depending on the stability of the blood protein target The processing of initial extract to obtain dried extract is the same as that described for dry milling in this section.

EXAMPLE 3

Concentration and Diafiltration of Recombinant Blood Protein and Control Rice Extracts.

The conditions used in concentration and diafiltration vary depending on volume, speed, cost, etc. These conditions are standard in the art based on the description herein. The frozen initial extract was thawed in the coldroom (about 2-8° C.) for six hours. The thawed material was clarified though a 0.45 μm filter and concentrated using a 5000 Nominal Molecular Weight Cutoff membrane of Polyethersultone.

90 ml of the filtrate of control extract was concentrated to 10 ml and additional 10 ml of deionized water can be added to the concentrated filtrate. The diluted filtrate can be diafiltrated one more time using water. The precipitate starts forming at 16 mS and increases as the ionic strength decreases. A solution of 1.0M ammonium bicarbonate was added to the retentate to add ionic strength. The haze decreases although does not disappear completely. The material was diafiltered multiple times, in one embodiment three times, with water and multiple times, in one embodiment three times, with 0.1 M ammonium bicarbonate. It was concentrated to 9 ml and the membrane is rinsed with 0.1 M ammonium bicarbonate. The concentrate was filtered through several 0.2 11 m button filters. In one embodiment, 2.3 ml of the filtrate is lyophilized as is; 2.3 ml of the filtrate is diluted to 12 ml with deionized water and lyophilized, and 2.0 ml of the filtrate is diluted to 25 ml with deionized water and lyophilized. All the filtrates remained clear.

A total of 89 ml of the filtrate of recombinant protein extract was concentrated to 10 ml, and additional 10 ml of 0.1 M ammonium bicarbonate is added. The resulting mixture is concentrated back to 10 ml and another 10 ml of 0.1 M ammonium bicarbonate is added. The retentate starts to haze up. The material was diafiltered multiple times, in one embodiment three times, with 0.1 M ammonium bicarbonate. It was concentrated to 9 ml and the membrane is rinsed with 0.1 M ammonium bicarbonate. The concentrate was filtered through several 0.45 μm button filters. In one embodiment, 2.0 ml of the filtrate was lyophilized as is; 2.0 ml of the filtrate was diluted to 12 ml with deionized water where a haze formed, and lyophilized, and 2.0 ml of the filtrate was diluted to 12 ml with 0.1 M ammonium bicarbonate that remained clear, and lyophilized.

EXAMPLE 4

Comparison of Trial Extraction of Recombinant Protein Rice with PBS and Ammonium Bicarbonate The conditions used in concentration and diafiltration vary depending on volume, speed, cost, etc. These conditions are all standard in the art based on the description herein. Recombinant protein rice flour is mixed with extraction buffer at about 100 g/L for about 1 hour using a magnetic stir bar. In one 2 L beaker, the extraction buffer is PBS, pH 7.4 plus 0.35 M NaCl. In another 2 L beaker, the extraction buffer is 0.5 M ammonium bicarbonate. A 15 cm Buchner funnel is pre-coated with about 6 g of Cel-pure C300 before adding another 20 g of Cel-pure C300. The mixture is filtered at about 3-4 Hg. It is then washed twice with about 100 nil of respective extraction buffer. The extracted filtrate is collected and concentrated with ultra-filtration cartridges: 5K Regenerate Cellulose, 5K PES, and 1K Regenerated Cellulose. The concentrates are lyophilized and analyzed for recombinant blood protein activity contents. The ammonium bicarbonate and PBS, pH 7.4 plus 0.35 M NaCl both extract approximately the same amount of rAAT. There is little loss of recombinant protein units in the permeate with any of the ultrafiltration units that were used, Other extraction buffer can also be used to extract recombinant proteins expressed in transgenic rice grains, for example Tris buffer, ammonium acetate, depending on applications.

EXAMPLE 5

Production of Rice Extracts Containing Recombinant Blood Proteins

The conditions used in concentration and diafiltration vary depending on volume, speed, cost, etc, These conditions are all standard in the art based on the description herein, All equipment is soaked in hot 0.1M NaOH at a starting temperature of about 55° C. Rice flour is added to an about 250-500 gal stainless steel tank containing 0.5M ammonium bicarbonate in a ratio of 95-105 g/L. It is mixed for about 60-80 minutes at about 9° C.

12 plates of 36 inch filter press C300 were pre-coated with about 3-6 kg Cel-pure C300. About 19-26 g/L of Cel-pure is added to the extract and mixed thoroughly. The mixture is pressed at a pressure of about 22 psi at a flow rate of about 82 liters/minute. The filtrate is collected into a 250 gal stainless steel tank and washed with 0.5M ammonium bicarbonate. The press is blown dry. This process is carried out at about 10° C.

The 300 NMW cut-off membranes (Polysulfone), which had been cleaned and stored with 0.1M NaOH after control run is rinsed thoroughly with deionized water. The extract is concentrated and bumped to a 100 gallon stainless steel tank. The membrane and the concentration tank were flushed with 0.1 M ammonium bicarbonate to recover all remaining extract. The products were covered with plastic and left in the 100 gallon tank overnight at room temperature. The concentrate is filtered through a spiral wound 1 μm filter and into a 5 gallon poly container.

EXAMPLE 6

Blending of Rice Extract Containing Recombinant Proteins into Parenteral, Inhalant, Intranasal and Topical Formulations.

Recombinant blood proteins (such as AAT) can be highly purified grains from cereal grains for use in medical/pharmaceutical applications. A purification protocol for rice seed extract expressed human AAT has been developed [Huang et al., 2002], consisting of preparing a rice seed extract according to the above examples and further purifying the extract preparation using Con-A, DEAE and Octyl Sepharose chromatography respectively. AAT can be purified to greater than 90% homogeneity utilizing such a procedure [Huang et al., 2002]. Purified AAT can be utilized in potential pharma/medical applications for the following indications: AAT augmentation/replacement therapy [Sandhaus, 1993; Hubbard et al., 1989], cystic fibrosis [McElvaney et al., 1991; Allen, 1996], psoriasis, panniculitis and cutaneous vasculitis [O'Riordan of al., 1997; Dowd et al., 1995] and pulmonary inflammation [Bingle and Tetley, 1996]. For some of these indications, purified AAT protein preparations can be administered via intravenous (iv) methods in 0.09% saline solution. Alternatively, the saline solution could be buffered with serum albumen at 0.5% or some other pharmacologically acceptable protein carrier molecule. AAT dosages are usually around 60 mg/kg. For aerosol delivery, an aerosol generating system can be employed utilizing a compressed air driven nebulizer selected on the basis of the basis of its ability to generate an aerosol with droplets of the optimum size (<3 um in aerodynamic diameter) for deposition in the lower respiratory tract [Hubbard of al., 1989). Again proteins can either be suspended in sterile water or a buffered saline solution containing a pharmacologically acceptable protein carrier. Alternatively, a dried protein powder containing the purified protein component could be utilized as the dispersal agent and this could be an a rice based extract where the AAT component is greater but not less then 50% by weight.

In another case, recombinant rice expressed and extracted human blood proteins such as AA T and fibrinogen can be employed topically. The use of fibrin sealants/bandages has been a widely accepted used by the medical community. Fibrin sealants are effective hemostatic agents [Mankad and Codispoti, 2001], a means for achieving tissue adhesion, preventing fluid accumulation and promotion of wound healing [Spotnitz, 2001]. Fibrin sealants can also be used as a means of slowly releasing medications, including antibiotics, growth factors and other agents [Spotnitz, 1997]. Rice expressed fibrinogen can also provide a potential low cost and animal virus free source for these indications.

What is claimed is:

1. A method of producing a recombinant human blood protein in monocot plant seeds, comprising the steps of:
   (a) transforming a monocot plant cell with a chimeric gene comprising
       (i) a promoter from the gene of a maturation-specific monocot plant storage protein operably linked to a first DNA sequence encoding a monocot plant seed-specific signal sequence capable of targeting a polypeptide linked thereto to a monocot plant seed endosperm cell, wherein the promoter operably linked to the sequence encoding the signal sequence comprises SEQ ID NO: 7; and
       (ii) a second DNA sequence encoding the human blood protein, linked in translation frame with the first DNA sequence, wherein the first DNA sequence and the second DNA sequence together encode a fusion protein comprising an N-terminal signal sequence and the human blood protein;
   (b) growing a monocot plant from the transformed monocot plant cell for a time sufficient to produce seeds containing the human blood protein; and
   (c) harvesting the seeds from the plant, wherein the human blood protein constitutes at least about 3.0% of the total soluble protein in the harvested seeds.

2. The method of claim 1, wherein the human blood protein is selected from the group consisting of hemoglobin, alpha-1-antitrypsin, fibrinogen, human serum albumin (HSA), thrombin, antithrombin Ill, an antibody, a growth factor and a blood coagulation factor.

3. The method of claim 1, wherein the human blood protein constitutes at least about 5.0% of the total soluble protein in the harvested seeds.

4. The method of claim 1, wherein the human blood protein constitutes at least about 10.0% of the total soluble protein in the harvested seeds.

5. The method of claim 1, further comprising purifying the human blood protein from the harvested seeds.

6. The method of claim 1, wherein the human blood protein produced in the method comprises one or more plant glycosyl groups.

7. A composition comprising a purified recombinant human blood protein obtained by the method of claim 1, wherein the human blood protein comprises one or more plant glycosyl groups; and wherein said composition comprises SEQ ID NO: 7.

8. The composition of claim 7, wherein the human blood protein is selected from the group consisting of hemoglobin, alpha-1-antitrypsin, fibrinogen, human serum albumin (HSA), thrombin, antithrombin III, an antibody, a growth factor and a blood coagulation factor.

9. A monocot plant seed product selected from the group consisting of whole seed, flour, extract, malt, and a partially purified protein fraction, prepared from the harvested seeds obtained by the method of claim 1, wherein the human blood protein constitutes at least about 3.0% of the total soluble protein in the seed product; and wherein the seed product comprises SEQ ID NO: 7.

10. The seed product of claim 9, wherein the human blood protein constitutes at least about 5.0% of the total soluble protein in the seed product.

11. The seed product of claim 9, wherein the human blood protein constitutes at least about 10.0% of the total soluble protein in the seed product.

12. The seed product of claim 9, wherein the human blood protein is selected from the group consisting of hemoglobin, alpha-1-antitrypsin, fibrinogen, human serum albumin (HSA), thrombin, antithrombin III, an antibody, a growth factor and a blood coagulation factor.

13. A composition comprising:
   a purified recombinant human blood protein obtained by the method of claim 1, wherein the human blood protein comprises one or more plant glycosyl groups; and
   at least one pharmaceutically acceptable excipient or nutrient from a source other than the monocot plant, wherein the excipient or nutrient is selected from the group consisting of salts, saccharides, vitamins, minerals, amino acids, peptides and proteins other than the human blood protein;
   wherein said composition comprises SEQ ID NO: 7.

14. The composition of claim 13, wherein the human blood protein is selected from the group consisting of hemoglobin, alpha-1-antitrypsin, fibrinogen, human serum albumin (HSA), thrombin, antithrombin Ill, an antibody, and a blood coagulation factor.

15. The composition of claim 13, wherein the composition is formulated for parenteral, enteric, inhalation, intranasal or topical delivery.

16. The composition of claim 13, wherein the composition is formulated for enteric delivery.

* * * * *

SEQUENCE LISTING

<160> NUMBER OF SEQ ID NOS: 21

<210> SEQ ID NO 1
<211> LENGTH: 1878
<212> TYPE: DNA
<213> ORGANISM: Artificial Sequence
<220> FEATURE:
<223> OTHER INFORMATION: Description of Artificial Sequence: Codon-
      optimized fibrinogen a-polypeptide coding sequence

<400> SEQUENCE: 1

| | | | | | | |
|---|---|---|---|---|---|---|
| gccgactccg | gcgagggcga | cttcctcgcc | gagggcggcg | gcgtccgggg | gccgcgcgtc | 60 |
| gtcgagcggc | accagtcggc | ctgcaaggac | tccgactggc | cgttctgctc | ggacgaggac | 120 |
| tggaactaca | agtgcccctc | cggctgccgc | atgaaggggc | tgatcgacga | ggtcaaccag | 180 |
| gacttcacca | accgcatcaa | caagctcaag | aactcgctgt | tcgagtacca | gaagaacaac | 240 |
| aaggactccc | actccctcac | gaccaacatc | atggagatcc | tgcgcggcga | cttctcctcc | 300 |
| gcgaacaacc | gcgacaacac | ctacaaccgc | gtctcggagg | acctccgctc | ccgcatcgag | 360 |
| gtcctgaagc | ggaaggtgat | cgagaaggtc | cagcacatcc | agctcctcca | aagaacgtc | 420 |
| cgcgcccagc | tcgtggacat | gaagcgcctg | gaggtggaca | tcgacatcaa | gatccggtcg | 480 |
| tgccgcggca | gctgctcccg | cgccctcgcc | cgcgaggtgg | acctcaagga | ctacgaggac | 540 |
| cagcagaagc | agctggagca | ggtcatcgcc | aaggacctcc | tcccgagccg | gaccggcag | 600 |
| cacctcccac | tgatcaagat | gaagccgtg | ccagacctgg | tccccggcaa | cttcaagagc | 660 |
| cagctccaga | aggtcccgcc | ggagtggaag | gccctcacgg | acatgcccca | aatgcgcatg | 720 |
| gagctggagc | gccccggcgg | caacgagatc | acgcgggggcg | gctccacctc | gtacggcacg | 780 |
| ggctccgaga | ccgagagccc | ccgcaacccc | tcctccgccg | gctcgtggaa | ctcggggtcc | 840 |
| agcggccccg | gttccacggg | caaccgcaac | cccggctcgt | ccggcaccgg | tggcaccgcc | 900 |
| acgtggaagc | caggtagctc | ggggccgggc | agcaccggca | gctggaactc | cggcagcagc | 960 |
| ggcaccggct | cgacgggcaa | ccagaacccg | ggcagccccc | gccccggctc | cacggggacc | 1020 |
| tggaacccag | gctcctccga | gcgggggtcc | gccggccact | ggacgagcga | gagctcggtg | 1080 |
| tcgggctcga | ccggccagtg | gcactcggaa | tccggcagct | tccggccaga | ctccccccggc | 1140 |
| agcggcaacg | cccggccgaa | caacccagac | tggggccacct | tcgaggaggt | ctccggtaac | 1200 |
| gtgagccccg | gcacgcgccg | ggagtaccac | acggagaagc | tggtgacgtc | gaagggcgac | 1260 |
| aaggagctcc | ggaccggcaa | ggagaaggtg | acctccggct | cgaccaccac | cacccggcgg | 1320 |
| tcctgctcga | agaccgtgac | gaagaccgtc | atcggtccgg | acggccacaa | ggaggtcacc | 1380 |
| aaggaggtgg | tcaccagcga | ggacggctcg | gactgcccgg | aggccatgga | cctgggcacc | 1440 |
| ctcagcggca | tcggcacgct | ggacggcttc | cgccaccggc | acccggacga | ggccgccttc | 1500 |
| ttcgacaccg | ctagcaccgg | caagaccttc | cccggtttct | tctcgccgat | gctcggcgag | 1560 |
| ttcgtgtccg | agacggagag | ccggggcagc | gagagtggca | tcttcaccaa | caccaaggaa | 1620 |
| tcctcctcgc | accacccagg | tatcgcggag | ttcccgagcc | ggggaagtc | ctcctcctac | 1680 |
| tccaagcagt | tcaccagctc | cacctcctac | aaccggggcg | acagcacgtt | cgagagcaag | 1740 |
| agctacaaga | tggccgacga | ggccggttcc | gaggccgacc | acgagggcac | ccactcgacg | 1800 |
| aagcgcgggc | acgccaagtc | gcgcccagtg | cgcgggatcc | acacgtcccc | gcgtcgcaag | 1860 |
| cccagcctgt | ccccgtga | | | | | 1878 |

```
<210> SEQ ID NO 2
<211> LENGTH: 1386
<212> TYPE: DNA
<213> ORGANISM: Artificial Sequence
<220> FEATURE:
<223> OTHER INFORMATION: Description of Artificial Sequence: Codon-
      optimized fibrinogen B-polypeptide coding sequence

<400> SEQUENCE: 2
caaggggtga acgacaacga ggagggtttc ttctccgccc gcggccaccg cccgctggac      60
aagaagcgcg aggaggcccc gagcctgcgc cccgcgcccc ccccatctc cggcggcggc     120 taccgggccc ggccggcaaa ggcggcggca acgcagaaga aggtcgagcg gaaggccccg     180
gacgccggcg gctgcctgca cgcggacccg gacctcggcg tcctgtgccc aacggggtgc     240
cagctccaag aggcgctcct ccaacaggag cgccccatcc ggaactccgt agacgagctg     300
aacaacaacg tggaggcagt gagccagacc tcctcgtcca gcttccagta catgtacctc     360
ctcaaggacc tctggcagaa gcggcaaaag caggtgaagg acaacgagaa cgtggtgaac     420
gagtacagct ccgagctcga aaagcaccag ctgtacatcg acgagaccgt gaactcgaac     480
atccccacga acctccgcgt cctgcgctcg atcctggaga acctccggag caagatccag     540
aagctagaat ccgacgtgtc ggcccagatg gagtattgcc ggaccccgtg caccgtcagc     600
tgcaacatcc cggtggtcag cggcaaggag tgcgaggaga tcatccgcaa gggcggcgag     660
accagcgaga tgtacctcat ccaacccgat tcctccgtca agccataccg ggtgtactgc     720
gacatgaaca cggagaacgg cgggtggacc gtgatccaga accgccagga cggctccgtg     780
gacttcggcc gcaagtggga cccgtacaag cagggcttcg gcaacgtggc cacgaacacg     840
gacgggaaga actactgcgg gctccccggc gaatactggc tggcaacga caagatctcc     900 cagctgaccc gcatgggccc caccgagctg ctcatcgaga tggaggactg gaagggcgac     960
aaggtgaagg cccactacgg gggcttcacg gtgcagaacg aggcgaacaa gtaccaaatc    1020
tcggtgaaca agtaccgcgg caccgctggg aacgcgctca tggacggcgc gagccagctg    1080
atgggcgaga accgcaccat gaccatccac aacggcatgt tcttcagcac ctacgaccgc    1140
gacaacgacg ggtggctcac gagcgacccc cggaagcagt gctcgaagga ggacggcggc    1200
ggctggtggt acaaccgctg ccacgcggca aaccccaacg tcgctacta ctggggcggt    1260 cagtacacgt gggacatggc gaagcacggc accgacgacg cgtcgtctg gatgaactgg    1320 aagggctcgt ggtacagcat gcggaagatg tccatgaaga tccgccccttt cttcccccag    1380 cagtga                                                                1386

<210> SEQ ID NO 3
<211> LENGTH: 1236
<212> TYPE: DNA
<213> ORGANISM: Artificial Sequence
<220> FEATURE:
<223> OTHER INFORMATION: Description of Artificial Sequence: Codon-
      optimized fibrinogen y-polypeptide encoding sequence

<400> SEQUENCE: 3
tacgtcgcca cccgggacaa ctgctgcatc ctggacgagc ggttcgggag ctactgccca      60
accacctgcg gcatcgccga cttcctgtcc acgtaccaga cgaaggtgga caaggacctc     120
cagtccctgg aggacatcct ccaccaggtg gagaacaaga cgtcggaggt caagcagctc     180
atcaaggcca tccagctcac ctacaacccg gacgaatcgt ccaagcccaa catgatcgac     240
gccgccaccc tcaagtcgcg gaagatgctg gaggagatca tgaagtacga ggcgtccatc     300
ctcacccacg actcctccat ccgctacctc caggagatct acaactccaa caaccaaaag     360
```

```
atcgtcaacc tcaaggagaa ggtcgcccag ctggaggcgc aatgccagga gccctgcaag      420
gacacggtgc aaatccacga catcacgggg aaggactgcc aagacatcgc caacaagggc      480
gccaagcaga gcgggctcta cttcatcaag cccctcaagg cgaaccagca gttcctggtc      540
tactgcgaga tcgacggctc gggcaacggc tggaccgtct tccagaagcg cctcgacggc      600
tccgtggact tcaagaagaa ctggatccaa tacaaggagg cttcggcca cctctccccc      660
accggcacga cggagttctg gctgggcaac gagaagatcc acctcatctc cacgcagagc      720
gcgatcccat acgccctccg ggtggagctg gaggactgga acggccgcac cagcaccgcg      780
gactacgcaa tgttcaaggt gggcccagag gcggacaagt accggctgac ctacgcctac      840
ttcgcgggcg gggacgcggg ggacgccttc gacgggttcg acttcggtga cgacccaagc      900
gacaagttct tcacgtccca caacggtatg cagttcagca cgtgggacaa cgacaacgac      960
aagttcgagg gtaactgcgc ggagcaggac ggcagcggct ggtggatgaa caagtgccac     1020
gcgggccacc tcaacggcgt ctactaccag ggcgggacct acagcaaggc atccacgcca     1080
aacgggtacg acaacggtat catctgggcc acgtggaaga cgcgctggta cagcatgaag     1140
aagaccacca tgaagatcat cccgttcaac cggctgacca tcggtgaggg ccagcagcac     1200
cacctcggcg gggccaagca ggcgggcgac gtgtga                               1236

<210> SEQ ID NO 4
<211> LENGTH: 1748
<212> TYPE: DNA
<213> ORGANISM: Homo sapiens

<400> SEQUENCE: 4
gatgcacaca agagtgaggt tgctcatcgg tttaaagatt tgggagaaga aaatttcaaa       60
gccttggtgt tgattgcctt tgctcagtat cttcagcagt gtccatttga agatcatgta      120
aaattagtga atgaagtaac tgaatttgca aaaacatgtg ttgctgatga gtcagctgaa      180
aattgtgaca atcacttcca tacccttttt ggagacaaat tatgcacagt tgcaactctt      240
cgtgaaacct atggtgaaat ggctgactgc tgtgcaaaac aagaacctga gagaaatgaa      300
tgcttcttgc aacacaaaga tgacaaccca aacctccccc gattggtgag accagaggtt      360
gatgtgatgt gcactgcttt tcatgacaat gaagagacat ttttgaaaaa atacttatat      420
gaaattgcca gaagacatcc ttacttttat gccccggaac tccttttctt tgctaaaagg      480
tataaagctg cttttacaga atgttgccaa gctgctgata agctgcctg cctgttgcca      540
aagctcgatg aacttcggga tgaagggaag gcttcgtctg ccaaacagag actcaagtgt      600
gccagtctcc aaaaatttgg agaaagagct ttcaaagcat gggcagtagc tcgcctgagc      660
cagagatttc ccaaagctga gtttgcagaa gttttccaagt tagtgacaga tcttaccaaa      720
gtccacacgg aatgctgcca tggagatctg cttgaatgtg ctgatgacag gcggaccttt      780
gccaagtata tctgtgaaaa tcaagattcg atctccagta aactgaagga atgctgtgaa      840
aaacctctgt tggaaaaatc ccactgcatt gccgaagtgg aaaatgatga tgatgcctgct      900
gacttgcctt cattagctgc tgattttgtt gaaagtaagg atgtttgcaa aaactatgct      960
gaggcaaagg atgtcttcct gggcatgttt ttatatgaat atgcaagaag gcatcctgat     1020
tactctgtcg tgctgctgct gagacttgcc aagacatatg aaaccactct agagaagtgc     1080
tgtgccgctg cagatcctca tgaatgctat gccaaagtgt tcgatgaatt taaacctctt     1140
gtggaagagc ctcagaattt aatcaaacaa aattgtgagc tttttgagca gcttggagag     1200
tacaaattcc agaatgcgct attagttcgt tacaccaaga agtaccccca agtgtcaact     1260
```

```
ccaactcttg tagaggtctc aagaaaccta ggaaaagtgg gcagcaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg atgaaacata cgttcccaaa    1500
gagtttaatg ctgaaacatt caccttccat gcagatatat gcacactttc tgagaaggag    1560
agacaaatca gaaacaaac tgcacttgtt gagcttgtga caaggcaaca aaagagcaac    1620
tgaaagctgt tatggatgat ttcgcagctt ttgtagagaa gtgctgcaag gctgacgata    1680
aggagacctg ctttgccgag gagggtaaaa aacttgttgc tgcaagtcaa gctgccttag    1740
gcttataa                                                             1748

<210> SEQ ID NO 5
<211> LENGTH: 1185
<212> TYPE: DNA
<213> ORGANISM: Artificial Sequence
<220> FEATURE:
<223> OTHER INFORMATION: Description of Artificial Sequence: Codon
      optimized alpha-1-antitrypsin coding sequence

<400> SEQUENCE: 5
gaggacccgc agggcgacgc cgcccagaag accgacacca gccaccacga ccaggaccac      60
ccgacgttca acaagatcac cccgaatttg gccgaattcg ccttcagcct gtaccgccag     120
ctcgcgcacc agtccaactc caccaacatc ttcttcagcc cggtgagcat cgccaccgcc     180
ttcgccatgc tgtccctggg taccaaggcg acacccacg acgagatcct cgaagggctg     240
aacttcaacc tgacggagat cccggaggcg cagatccacg agggcttcca ggagctgctc     300
aggacgctca accagccgga ctcccagctc cagctcacca ccggcaacgg gctcttcctg     360
tccgagggcc tcaagctcgt cgataagttc ctggaggacg tgaagaagct ctaccactcc     420
gaggcgttca ccgtcaactt cggggacacc gaggaggcca agaagcagat caacgactac     480
gtcgagaagg ggacccaggg caagatcgtg gacctggtca aggaattgga cagggacacc     540
gtcttcgcgc tcgtcaacta catcttcttc aagggcaagt gggagcgccc gttcgaggtg     600
aaggacaccg aggaggagga cttccacgtc gaccaggtca ccaccgtcaa ggtcccgatg     660
atgaagaggc tcggcatgtt caacatccag cactgcaaga agctctccag ctgggtgctc     720
ctcatgaagt acctggggaa cgccaccgcc atcttcttcc tgccggacga gggcaagctc     780
cagcacctgg agaacgagct gacgcacgac atcatcacga agttcctgga gaacgaggac     840
aggcgctccg ctagcctcca cctcccgaag ctgagcatca ccggcacgta cgacctgaag     900
agcgtgctgg ccagctggg catcacgaag gtcttcagca acggcgcgga cctctccggc     960
gtgacggagg aggcccccct gaagctctcc aaggccgtgc acaaggcggt gctcacgatc    1020
gacgagaagg gacggaagc tgccgggggcc atgttcctgg aggccatccc cgtgtccatc    1080
ccgcccgagg tcaagttcaa caagcccttc gtcttcctga tgatcgagca gaacacgaag    1140
agccccctct tcatggggaa ggtcgtcaac cccacgcaga agtga                    1185

<210> SEQ ID NO 6
<211> LENGTH: 786
<212> TYPE: DNA
<213> ORGANISM: Oryza sp.

<400> SEQUENCE: 6
catgagtaat gtgtgagcat tatgggacca cgaaataaaa agaacatttt gatgagtcgt      60
```

-continued

```
gtatcctcga tgagcctcaa aagttctctc accccggata agaaacccctt aagcaatgtg    120 caaagtttgc attctccact gacataatgc aaaataagat atcatcgatg acatagcaac    180
tcatgcatca tatcatgcct ctctcaacct attcattcct actcatctac ataagtatct    240
tcagctaaat gttagaacat aaacccataa gtcacgtttg atgagtatta ggcgtgacac    300
atgacaaatc acagactcaa gcaagataaa gcaaatgat gtgtacataa aactccagag     360
ctatatgtca tattgcaaaa agaggagagc ttataagaca aggcatgact cacaaaaatt    420
cacttgcctt tcgtgtcaaa agaggaggg ctttacatta tccatgtcat attgcaaaag     480
aaagagagaa agaacaacac aatgctgcgt caattataca tatctgtatg tccatcatta    540
ttcatccacc tttcgtgtac cacacttcat atatcataag agtcacttca cgtctggaca    600
ttaacaaact ctatcttaac atttagatgc aagagccttt atctcactat aaatgcacga    660
tgatttctca ttgtttctca caaaaagcgg ccgcttcatt agtcctacaa caacatggca    720
tccataaatc gccccatagt tttcttcaca gtttgcttgt tcctcttgtg cgatggctcc    780
ctagcc                                                               786
```

<210> SEQ ID NO 7
<211> LENGTH: 1055
<212> TYPE: DNA
<213> ORGANISM: Oryza sp.

<400> SEQUENCE: 7

```
ctgcagggag gagaggggag agatggtgag agaggaggaa gaagaggagg ggtgacaatg     60
atatgtgggg catgtgggca cccaattttt taattcattc ttttgttgaa actgacatgt    120
gggtcccatg agatttatta tttttcggat cgaatcgcca cgtaagcgct acgtcaatgc    180
tacgtcagat gaagaccgag tcaaattagc cacgtaagcg ccacgtcagc caaaaccacc    240
atccaaaccg ccgagggacc tcatctgcac tggttttgat agttgaggga cccgttgtat    300 ctggttttc gattgaagga cgaaaatcaa atttgttgac aagttaaggg accttaaatg     360
aacttattcc atttcaaaat attctgtgag ccatatatac cgtgggcttc caatcctcct    420
caaattaaag ggcctttta aaatagataa ttgccttctt tcagtcaccc ataaaagtac     480
aaaactacta ccaacaagca acatgcgcag ttacacacat tttctgcaca tttccgccac    540
gtcacaaaga gctaagagtt atccctagga caatctcatt agtgtagata catccattaa    600
tcttttatca gaggcaaacg taaagccgct ctttatgaca aaaataggtg acacaaaagt    660
gttatctgcc acatacataa cttcagaaat tacccaacac caagagaaaa ataaaaaaaa    720 atcttttgc aagctccaaa tcttggaaac cttttttcact cttttgcagca ttgtactctt    780 gctcttttc caaccgatcc atgtcaccct caagcttcta cttgatctac acgaagctca    840
ccgtgcacac aaccatggcc acaaaaaccc tataaaaccc catccgatcg ccatcatctc    900
atcatcagtt cattaccaac aaacaaaaga ggaaaaaaaa catatacact tctagtgatt    960
gtctgattga tcatcaatct agaggcggcc gcatggctag caaggtcgtc ttcttcgcgg   1020
cggcgctcat ggcggccatg gtggccatct ccggc                              1055
```

<210> SEQ ID NO 8
<211> LENGTH: 976
<212> TYPE: DNA
<213> ORGANISM: Triticum sp.

<400> SEQUENCE: 8

```
ctgcaggcca gggaaagaca atggacatgc aaagaggtag gggcagggaa gaaacacttg     60
```

| | |
|---|---|
| gagatcatag aagaacataa gaggttaaac ataggagggc ataatggaca attaaatcta | 120 |
| cattaattga actcatttgg gaagtaaaca aaatccatat tctggtgtaa atcaaactat | 180 |
| ttgacgcgga tttactaaga tcctatgtta attttagaca tgactggcca aaggtttcag | 240 |
| ttagttcatt tgtcacggaa aggtgttttc ataagtccaa aactctacca acttttttgc | 300 |
| acgtcatagc atagatagat gttgtgagtc attggataga tattgtgagt cagcatggat | 360 |
| ttgtgttgcc tggaaatcca actaaatgac aagcaacaaa acctgaaatg ggctttagga | 420 |
| gagatggttt atcaatttac atgttccatg caggctacct tccactactc gacatggtta | 480 |
| gaagttttga gtgccgcata tttgcggaag caatggcact actcgacatg gttagaagtt | 540 |
| ttgagtgccg catatttgcg gaagcaatgg ctaacagata catattctgc caaaccccaa | 600 |
| gaaggataat cactcctctt agataaaaag aacagaccaa tgtacaaaca tccacacttc | 660 |
| tgcaaacaat acaccagaac taggattaag cccattacgt ggctttagca gaccgtccaa | 720 |
| aaatctgttt tgcaagcacc aattgctcct tacttatcca gcttcttttg tgttggcaaa | 780 |
| ctgccctttt ccaaccgatt tgtttcttc tcacgctttc ttcataggct aaactaacct | 840 |
| cggcgtgcac acaaccatgt cctgaacctt cacctcgtcc ctataaaagc ccatccaacc | 900 |
| ttacaatctc atcatcaccc acaacaccga gcaccccaat ctacagatca attcactgac | 960 |
| agttcactga tctaga | 976 |

<210> SEQ ID NO 9
<211> LENGTH: 1009
<212> TYPE: DNA
<213> ORGANISM: Oryza sp.

<400> SEQUENCE: 9

| | |
|---|---|
| ctgcagtaat ggatacctag tagcaagcta gcttaaacaa atctaaattc caatctgttc | 60 |
| gtaaacgttt tctcgatcgc aattttgatc aaaactattg aaaacctcaa ttaaaccatt | 120 |
| caaaatttt aatatacccca acaagagcgt ccaaaccaaa tatgtaaata tggatgtcat | 180 |
| gataattgac ttatgacaat gtgattattt catcaagtct ttaaatcatt aattctagtt | 240 |
| gaaggtttat gttttcttat gctaagggt tatgtttata taagaatatt aaagagcaaa | 300 |
| ttgcaataga tcaacacaac aaatttgaat gtttccagat gtgtaaaaat atccaaatta | 360 |
| attgtttta aatagtttta agaaggatct gatatgcaag tttgatagtt agtaaactgc | 420 |
| aaaagggctt attacatgga aaattcctta ttgaatatgt tcattgact ggtttatttt | 480 |
| acatgacaac aaagttacta gtatgtcaat aaaaaaatac aaggttactt gtcaattgta | 540 |
| ttgtgccaag taagatgac aacaaacata caaatttatt tgttctttta tagaaacacc | 600 |
| taacttatca aggatagttg gccacgcaaa aatgacaaca tactttacaa ttgtatcatc | 660 |
| ataaagatct tatcaagtat aagaacttta tggtgacata aaaaataatc acaagggcaa | 720 |
| gacacatact aaaagtatgg acagaaattt cttaacaaac tccatttgtt ttgtatccaa | 780 |
| aagcataaga aatgagtcat ggctgagtca tgatatgtag ttcaatcttg caaaattgcc | 840 |
| tttttgttaa gtattgtttt aacactacaa gtcacatatt gtctatactt gcaacaaaca | 900 |
| ctattaccgt gtatcccaag tggccttttc attgctatat aaactagctt gatcggtctt | 960 |
| tcaactcaca tcaattagct taagtttcca ttagcaactg ctaatagct | 1009 |

<210> SEQ ID NO 10
<211> LENGTH: 839
<212> TYPE: DNA
<213> ORGANISM: Oryza sp.

```
<400> SEQUENCE: 10
ctgcagtgta agtgtagctt cttatagctt agtgctttac tatcttcaca agcacatgct      60
atagtattgt tccaagatga aagaataatt catccttgct accaacttgc atgatattat     120
atttgtgaat atcctatctc ttggcttata atgaaatgtg ctgctgggtt attctgacca     180
tggtatttga gagcctttgt atagctgaaa ccaacgtata tcgagcatgg aacagagaac     240
aaaatgcaag gatttttta ttctggttca tgccctggat gggttaatat cgtgatcatc      300
aaaaaagata tgcataaaat taaagtaata aatttgctca taagaaacca aaaccaaaag     360
cacatatgtc ctaaacaaac tgcattttgt ttgtcatgta gcaatacaag agataatata     420
tgacgtggtt atgacttatt cacttttgt gactccaaaa tgtagtaggt ctaactgatt      480
gtttaaagtg atgtcttact gtagaagttt catcccaaaa gcaatcacta agcaacaca      540 cacgtatagt ccaccttcac gtaattcttt gtggaagata acaagaaggc tcactgaaaa     600
ataaaagcaa agaaaaggat atcaaacaga ccattgtgca tcccattgat ccttgtatgt     660
ctatttatct atcctccttt tgtgtacctt acttctatct agtgagtcac ttcatatgtg     720
gacattaaca aactctatct taacatctag tcgatcacta ctttacttca ctataaaagg     780
accaacatat atcatccatt tctcacaaaa gcattgagtt cagtcccaca aaatctaga      839

<210> SEQ ID NO 11
<211> LENGTH: 1302
<212> TYPE: DNA
<213> ORGANISM: Oryza sp.

<400> SEQUENCE: 11
ctgcagagat atggattttc taagattaat tgattctctg tctaaagaaa aaagtattta      60
ttgaattaaa tggaaaaaga aaaggaaaa aggggatggc ttctgctttt tgggctgaag     120
gcggcgtgtg ccagcgtgc tgcgtgcgga cagcgagcga acacacgacg gagcagctac     180
gacgaacggg ggaccgagtg gaccggacga ggatgtggcc taggacgagt gcacaaggct     240
agtggactcg gtccccgcgc ggtatcccga gtggtccact gtctgcaaac acgattcaca     300
tagagcgggc agacgcggga gccgtcctag gtgcaccgga agcaaatccg tcgcctgggt     360
ggatttgagt gacacggccc acgtgtagcc tcacagctct ccgtggtcag atgtgtaaaa     420
ttatcataat atgtgttttt caaatagtta ataatatat ataggcaagt tatatgggtc      480
aataagcagt aaaaaggctt atgacatggt aaaattactt acaccaatat gccttactgt     540
ctgatatatt ttacatgaca acaaagttac aagtacgtca tttaaaaata caagttactt     600
atcaattgta gtgtatcaag taaatgacaa caaacctaca aatttgctat tttgaaggaa     660
cacttaaaaa aatcaatagg caagttatat agtcaataaa ctgcaagaag cttatgaca      720 tggaaaaatt acatacacca atatgcttta ttgtccggta tattttacaa gacaacaaag     780
ttataagtat gtcatttaaa aatacaagtt acttatcaat tgtcaagtaa atgaaaacaa     840
acctacaaat ttgttatttt gaaggaacac ctaaattatc aaatatagct tgctacgcaa     900
aatgacaaca tgcttacaag ttattatcat cttaaagtta gactcatctt ctcaagcata     960
agagctttat ggtgcaaaaa caaatataat gacaaggcaa agatacatac atattaagag    1020
tatggacaga catttcttta acaaactcca tttgtattac tccaaaagca ccagaagttt    1080
gtcatggctg agtcatgaaa tgtatagttc aatcttgcaa agttgccttt ccttttgtac    1140
tgtgttttaa cactacaagc catatattgt ctgtacgtgc aacaaactat atcaccatgt    1200
atcccaagat gctttttat tgctatataa actagcttgg tctgtctttg aactcacatc     1260
```

| | |
|---|---|
| aattagctta agtttccata agcaagtaca aatagctcta ga | 1302 |

<210> SEQ ID NO 12
<211> LENGTH: 675
<212> TYPE: DNA
<213> ORGANISM: Oryza sp.

<400> SEQUENCE: 12

| | |
|---|---|
| ctgcagcatc ggcttaggtg tagcaacacg actttattat tattattatt attattatta | 60 |
| ttattttaca aaaatataaa atagatcagt ccctcaccac aagtagagca agttggtgag | 120 |
| ttattgtaaa gttctacaaa gctaatttaa aagttattgc attaacttat ttcatattac | 180 |
| aaacaagagt gtcaatggaa caatgaaaac catatgacat actataattt tgttttatt | 240 |
| attgaaatta tataattcaa agagaataaa tccacatagc cgtaaagttc tacatgtggt | 300 |
| gcattaccaa aatatatata gcttacaaaa catgacaagc ttagtttgaa aaattgcaat | 360 |
| ccttatcaca ttgacacata aagtgagtga tgagtcataa tattatttt cttgctaccc | 420 |
| atcatgtata tatgatagcc acaaagttac tttgatgatg atatcaaaga acattttag | 480 |
| gtgcacctaa cagaatatcc aaataatatg actcacttag atcataatag agcatcaagt | 540 |
| aaaactaaca ctctaaagca accgatggga aagcatctat aaatagacaa gcacaatgaa | 600 |
| aatcctcatc atccttcacc acaattcaaa tattatagtt gaagcatagt agtagaatcc | 660 |
| aacaacaatc tagag | 675 |

<210> SEQ ID NO 13
<211> LENGTH: 1098
<212> TYPE: DNA
<213> ORGANISM: Oryza sp.

<400> SEQUENCE: 13

| | |
|---|---|
| ccaggcttca tcctaaccat tacaggcaag atgttgtatg aagaagggcg aacatgcaga | 60 |
| ttgttaaact gacacgtgat ggacaagaat gaccgattgg tgaccggtct gacaatggtc | 120 |
| atgtcgtcag cagacagcca tctcccacgt cgcgcctgct tccggtgaaa gtggaggtag | 180 |
| gtatgggccg tcccgtcaga aggtgattcg gatggcagcg atacaaatct ccgtccatta | 240 |
| atgaagagaa gtcaagttga aagaagggga gggagagatg gtgcatgtgg gatcccttg | 300 |
| ggatataaaa ggaggacctt gcccacttag aaaggagagg agaaagcaat cccagaagaa | 360 |
| tcggggggctg actggcactt tgtagcttct tcatacgcga atccaccaaa acacaggagt | 420 |
| agggtattac gcttctcagc ggcccgaacc tgtatacatc gcccgtgtct tgtgtgtttc | 480 |
| cgctcttgcg aaccttccac agattgggag cttagaacct cacccagggc ccccggccga | 540 |
| actggcaaag gggggcctgc gcggtctccc ggtgaggagc cccacgctcc gtcagttcta | 600 |
| aattacccga tgagaaaggg agggggggggg gggaaatctg ccttgtttat ttacgatcca | 660 |
| acggatttgg tcgacaccga tgaggtgtct taccagttac cacgagctag attatagtac | 720 |
| taattacttg aggattcggt tcctaatttt ttacccgatc gacttcgcca tggaaaattt | 780 |
| tttattcggg ggagaatatc caccctgttt cgctcctaat taagatagga attgttacga | 840 |
| ttagcaacct aattcagatc agaattgtta gttagcggcg ttggatccct cacctcatcc | 900 |
| catcccaatt cccaaaccca aactcctctt ccagtcgccg acccaaacac gcatccgccg | 960 |
| cctataaatc ccacccgcat cgagcctatc aagcccaaaa aaccacaaac caaacgaaga | 1020 |
| aggaaaaaaa aaggaggaaa agaaaagagg aggaaagcga agaggttgga gagagacgct | 1080 |
| cgtctccacg tcgccgcc | 1098 |

<210> SEQ ID NO 14
<211> LENGTH: 432
<212> TYPE: DNA
<213> ORGANISM: Hordeum sp.

<400> SEQUENCE: 14

```
cttcgagtgc cgccgattt gccagcaatg gctaacagac acatattctg ccaaaacccc      60
agaacaataa tcacttctcg tagatgaaga gaacagacca agatacaaac gtccacgctt     120
cagcaaacag taccccagaa ctaggattaa gccgattacg cggctttagc agaccgtcca    180
aaaaaactgt tttgcaaagc tccaattcct ccttgcttat ccaatttctt ttgtgttggc    240
aaactgcact tgtccaaccg attttgttct tcccgtgttt cttcttaggc taactaacac    300
agccgtgcac atagccatgg tccggaatct tcacctcgtc cctataaaag cccagccaat    360
ctccacaatc tcatcatcac cgagaacacc gagaaccaca aaactagaga tcaattcatt    420
gacagtccac cg                                                         432
```

<210> SEQ ID NO 15
<211> LENGTH: 60
<212> TYPE: DNA
<213> ORGANISM: Triticum sp.

<400> SEQUENCE: 15

```
atggctaagc gcctggtcct ctttgcggca gtagtcgtcg ccctcgtggc tctcaccgcc     60
```

<210> SEQ ID NO 16
<211> LENGTH: 72
<212> TYPE: DNA
<213> ORGANISM: Oryza sp.

<400> SEQUENCE: 16

```
atggcaacta ccatttctc tcgttttct atatactttt gtgctatgct attatgccag       60
ggttctatgg cc                                                          72
```

<210> SEQ ID NO 17
<211> LENGTH: 85
<212> TYPE: DNA
<213> ORGANISM: Oryza sp.

<400> SEQUENCE: 17

```
atgtggacat taacaaactc tatcttaaca tctagtcgat cactacttta cttcactata     60
aaaggaccaa catatatcat ccatt                                           85
```

<210> SEQ ID NO 18
<211> LENGTH: 72
<212> TYPE: DNA
<213> ORGANISM: Oryza sp.

<400> SEQUENCE: 18

```
atggcgagtt ccgttttctc tcggttttct atatactttt gtgttcttct attatgccat     60
ggttctatgg cc                                                          72
```

<210> SEQ ID NO 19
<211> LENGTH: 69
<212> TYPE: DNA
<213> ORGANISM: Oryza sp.

<400> SEQUENCE: 19

```
atgaagatca ttttcgtatt tgctctcctt gctattgttg catgcaacgc ttctgcacgg     60
```

```
                                        -continued
tttgatgct                                                                  69

<210> SEQ ID NO 20
<211> LENGTH: 63
<212> TYPE: DNA
<213> ORGANISM: Oryza sp.

<400> SEQUENCE: 20
atggccgccc gcgccgccgc cgccgcgttc ctgctgctgc tcatcgtcgt tggtcaccgc           60
gcc                                                                        63

<210> SEQ ID NO 21
<211> LENGTH: 63
<212> TYPE: DNA
<213> ORGANISM: Hordeum sp.

<400> SEQUENCE: 21
atggctaagc ggctggtcct ctttgtggcg gtaatcgtcg ccctcgtggc tctcaccacc           60
gcc                                                                        63
```